(12) United States Patent
Henke et al.

(10) Patent No.: US 12,171,589 B2
(45) Date of Patent: Dec. 24, 2024

(54) MEDICAL PACKAGING DEVICE, MEDICAL PACKAGING SYSTEM, METHOD FOR PRODUCING A MEDICAL PACKAGING DEVICE, AND METHOD FOR STERILE PACKING OF A STRAINER BASKET

(71) Applicant: Aesculap AG, Tuttlingen (DE)

(72) Inventors: Matthias Henke, Villingen-Schwenningen (DE); Philipp Bohnenstengel, Steisslingen (DE)

(73) Assignee: Aesculap AG, Tuttlingen (DE)

( * ) Notice: Subject to any disclaimer, the term of this patent is extended or adjusted under 35 U.S.C. 154(b) by 30 days.

(21) Appl. No.: 18/329,742

(22) Filed: Jun. 6, 2023

(65) Prior Publication Data

US 2023/0310110 A1    Oct. 5, 2023

Related U.S. Application Data

(63) Continuation of application No. PCT/EP2021/081330, filed on Nov. 11, 2021.

(30) Foreign Application Priority Data

Dec. 7, 2020   (DE) ..................... 10 2020 132 419.7

(51) Int. Cl.
    *B65D 75/04*   (2006.01)
    *A61B 50/34*   (2016.01)
    (Continued)

(52) U.S. Cl.
    CPC ............... *A61B 50/34* (2016.02); *A61L 2/07* (2013.01); *A61L 2/26* (2013.01); *B65D 75/04* (2013.01);
    (Continued)

(58) Field of Classification Search
    CPC .............. A61B 50/34; A61B 2050/002; A61B 2050/314; A61L 2/07; A61L 2/26; A61L 2202/181; A61L 2202/24; B65D 75/04
    (Continued)

(56) References Cited

U.S. PATENT DOCUMENTS

| 2,265,680 A | 12/1941 | Alberta |
| 3,680,772 A | 8/1972 | Hoover |

(Continued)

FOREIGN PATENT DOCUMENTS

| AU | 2015224419 B2 | 11/2016 |
| EP | 2992851 A1 | 3/2016 |
| JP | 07215369 A | 8/1995 |

*Primary Examiner* — Jacob K Ackun
(74) *Attorney, Agent, or Firm* — Christopher A. Rothe; CM Law

(57) ABSTRACT

A medical packaging device, packaging system, method for producing a packaging device, and method for sterile packaging of a sieve basket with a packaging device. The packaging device defines a receiving space for accommodating a sieve basket in a packaging position, and an insertion opening for inserting a sieve basket into the receiving space. The insertion opening is open in an insertion position. The packaging device is made from a flat material sheet that is folded multiple times. The receiving space has two abutting receiving space flat material sheet surface regions. The regions are delimited by at least three fold lines of the flat material sheet such that the receiving space is closed on all sides except for the insertion opening. The packaging device includes an unfolding securing device for securing the packaging device in the insertion position against being completely unfolded back into the starting position.

19 Claims, 10 Drawing Sheets

(51) Int. Cl.
*A61L 2/07* (2006.01)
*A61L 2/26* (2006.01)
*A61B 50/00* (2016.01)
*A61B 50/30* (2016.01)

(52) U.S. Cl.
CPC ... *A61B 2050/002* (2016.02); *A61B 2050/314* (2016.02); *A61L 2202/181* (2013.01); *A61L 2202/24* (2013.01)

(58) Field of Classification Search
USPC ........................................................ 206/438
See application file for complete search history.

(56) References Cited

U.S. PATENT DOCUMENTS

| | | | |
|---|---|---|---|
| 4,705,171 | A | 11/1987 | Eldridge |
| 5,447,230 | A | 9/1995 | Gerondale |
| 8,685,189 | B2 | 4/2014 | Pamperin et al. |
| 9,174,782 | B2 | 11/2015 | Gaynor et al. |
| 2002/0092274 | A1 | 7/2002 | Banks |
| 2007/0026472 | A1 | 2/2007 | Prokash et al. |
| 2012/0195792 | A1* | 8/2012 | Duddy ............... A61L 2/26 422/28 |
| 2013/0112589 | A1 | 5/2013 | Lien et al. |
| 2016/0073862 | A1* | 3/2016 | Matsuno .......... A61B 18/1492 206/370 |
| 2019/0021806 | A1* | 1/2019 | Turbett ............. A61B 46/40 |
| 2020/0407142 | A1* | 12/2020 | Wolf ................. B65D 77/003 |
| 2022/0024664 | A1* | 1/2022 | Allard .............. B65D 75/58 |
| 2023/0094714 | A1* | 3/2023 | Banerjee ............ A61B 42/40 604/540 |
| 2024/0033181 | A1* | 2/2024 | Wolf ................. B32B 27/16 |

* cited by examiner

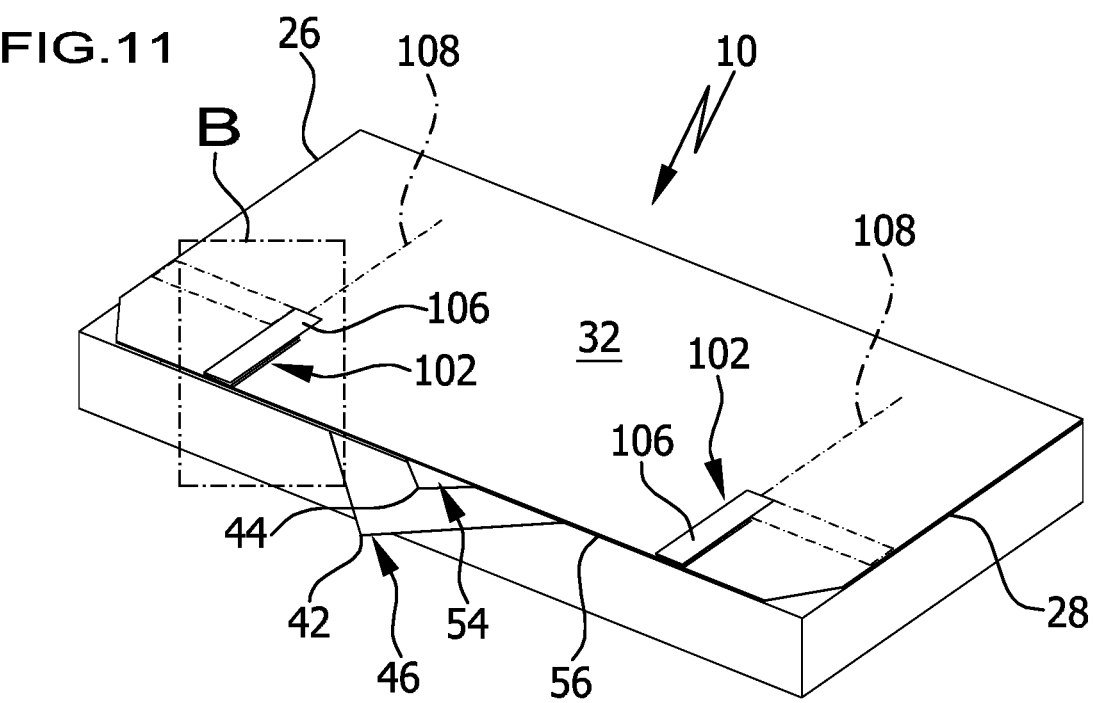
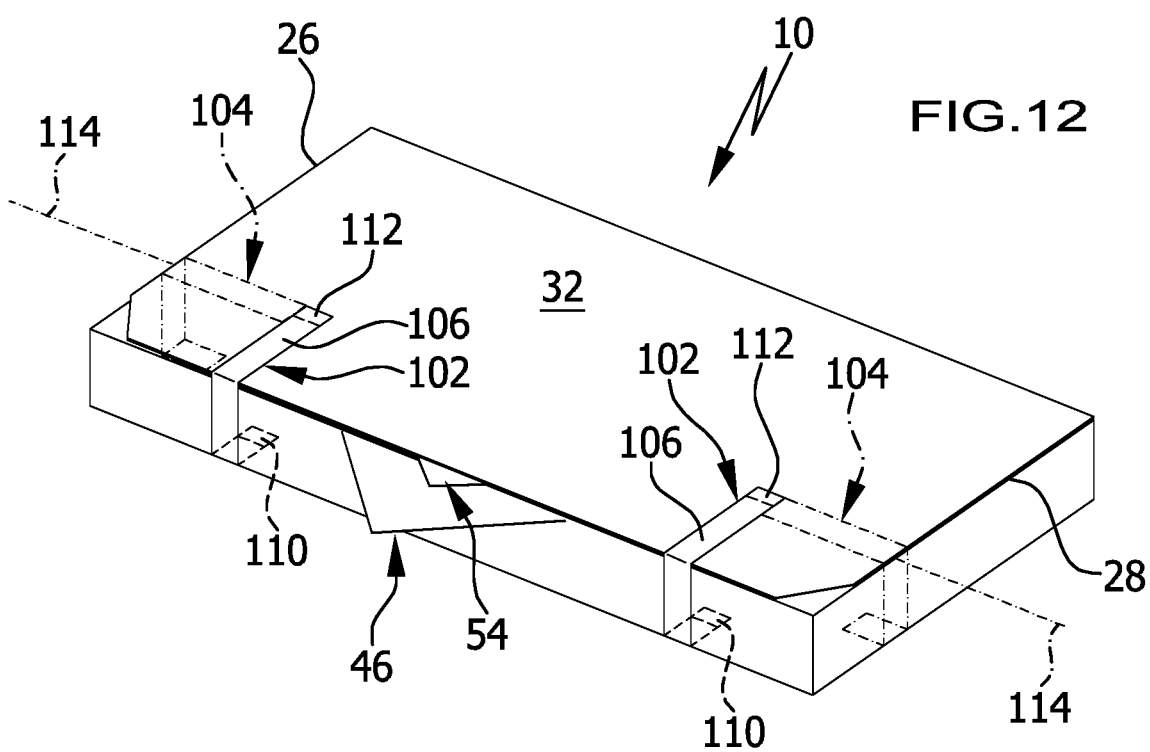

FIG.16
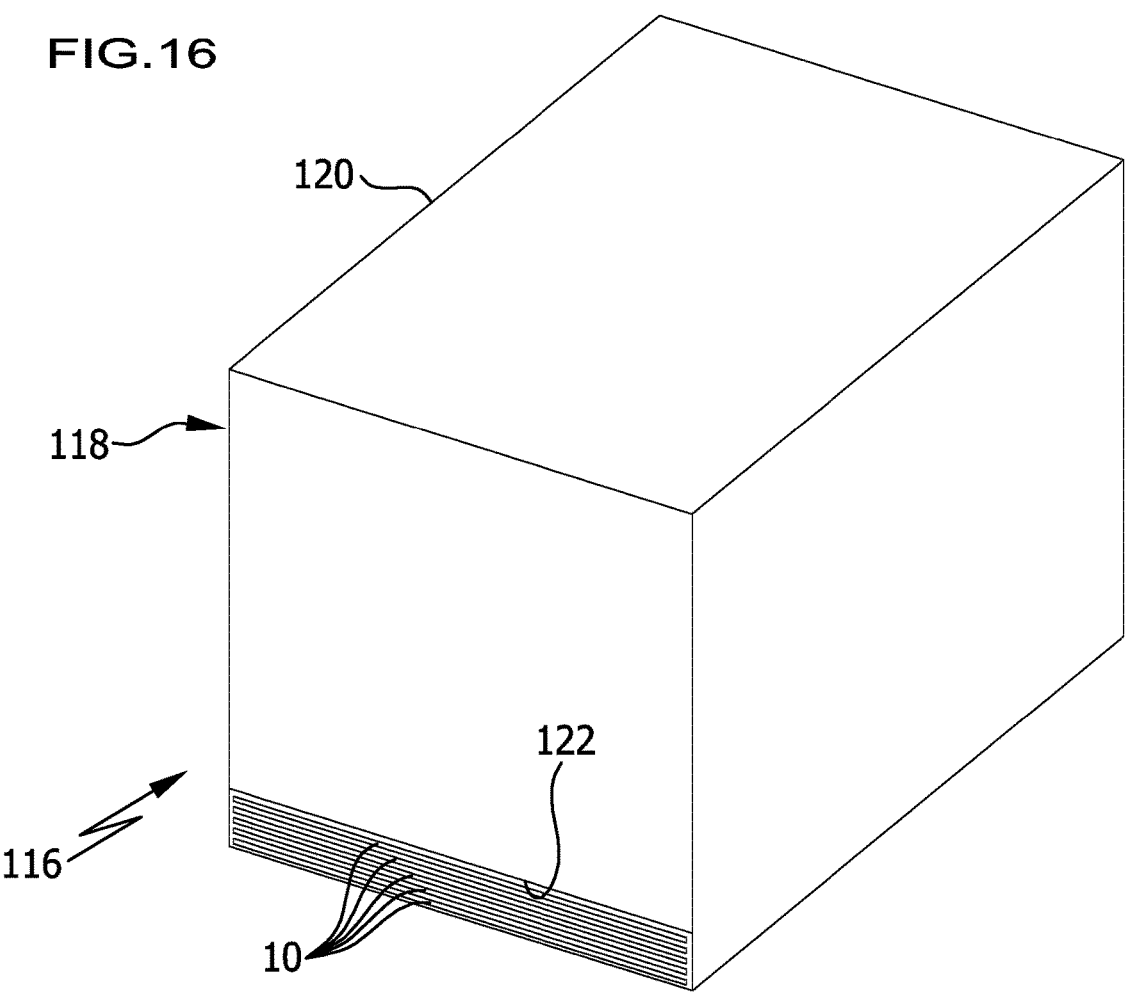
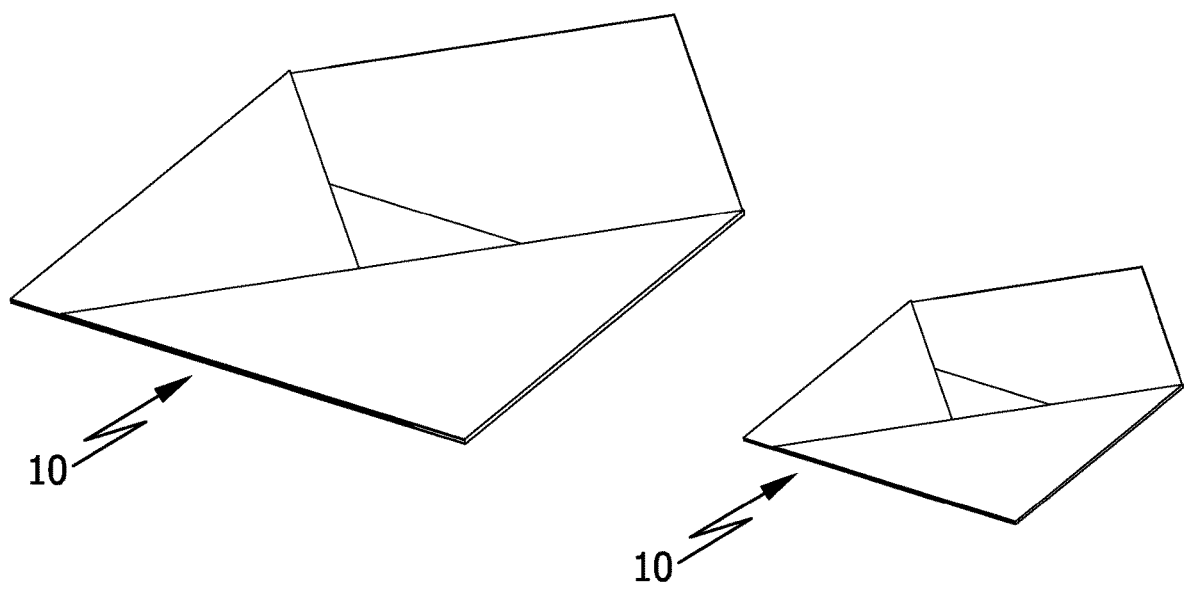

MEDICAL PACKAGING DEVICE, MEDICAL PACKAGING SYSTEM, METHOD FOR PRODUCING A MEDICAL PACKAGING DEVICE, AND METHOD FOR STERILE PACKING OF A STRAINER BASKET

CROSS-REFERENCE TO RELATED APPLICATIONS

This application is a continuation of International Application No. PCT/EP2021/081330, filed on Nov. 11, 2021 and claims priority to German Application No. 10 2020 132 419.7, filed on Dec. 7, 2020. The contents of International Application No. PCT/EP2021/081330 and German Application No. 10 2020 132 419.7 are incorporated by reference herein in their entireties and for all purposes.

FIELD

The present disclosure relates to medical packaging devices generally, and more specifically to a medical packaging device for sterile packaging of a sieve basket, wherein the packaging device defines a receiving space for accommodating a sieve basket in a packaging position and an insertion opening for inserting a sieve basket into the receiving space, wherein the insertion opening is open in an insertion position, wherein the packaging device is made from a flat material sheet that is unfolded in a starting position by folding multiple times, wherein the receiving space in the insertion position has two abutting receiving space flat material sheet surface regions, which are delimited by at least three fold lines of the flat material sheet in such a way that the receiving space is closed on all sides except for the insertion opening.

Furthermore, the present disclosure relates to medical packaging systems generally, and more specifically to a medical packaging system for sieve baskets.

Moreover, the present disclosure relates to methods for producing a medical packaging device for sterile packaging of a sieve basket generally, and more specifically to a method for producing a medical packaging device for sterile packaging of a sieve basket, wherein the packaging device is configured with a receiving space for accommodating a sieve basket in a packaging position and an insertion opening for inserting a sieve basket into the receiving space, wherein the insertion opening is open in an insertion position, wherein the packaging device is made from a flat material sheet that is unfolded in a starting position by folding multiple times, wherein the receiving space in the insertion position has two abutting receiving space flat material sheet surface regions, which are delimited by at least three fold lines of the flat material sheet in such a way that the receiving space is closed on all sides except for the insertion opening.

Furthermore, the present disclosure relates to a method for sterile packaging of a sieve basket with a medical packaging device.

BACKGROUND

Sieve baskets or sterilization sieve trays are typically wrapped in non-woven cloths after being loaded with instruments or implants before they are sterilized. This requires large non-woven cloths. After being wrapped in a non-woven cloth, a sieve basket is thus surrounded by a soft packaging, formed by the non-woven cloth. In a next step, the packaged sieve baskets are introduced into a sterilization container and sterilized therein, in particular sterilized with hot steam.

The expenditure required to surround the sieve baskets with a soft packaging in the described manner is very large. The non-woven cloths provided in the form of sheets must be stored, in particular, without damage. Furthermore, employees must be trained in different folding techniques in order to completely wrap the sieve basket in the non-woven cloth. Here, sieve baskets may often be packaged incorrectly, which is associated with the risk that the desired sterility of the sieve basket and its contents is not always ensured.

It is known, in particular, to wrap sieve baskets in a diagonal packaging or a parallel packaging in accordance with DIN 58953-7. To do so requires many manual folding steps to correctly wrap the sieve basket in the non-woven cloth. This is associated with a high expenditure for training the staff that performs the packaging step. Independent of this, the quality of the packaging of the sieve basket ultimately depends on the respective employee. High costs arise for the packaging of the sieve basket due to the high time expenditure.

SUMMARY

In a first aspect of the present disclosure, a medical packaging device for sterile packaging of a sieve basket is provided. The packaging device defines a receiving space for accommodating a sieve basket in a packaging position and an insertion opening for inserting a sieve basket into the receiving space. The insertion opening is open in an insertion position. The packaging device is made from a flat material sheet that is unfolded in a starting position by folding multiple times. The receiving space in the insertion position has two abutting receiving space flat material sheet surface regions, which are delimited by at least three fold lines of the flat material sheet in such a way that the receiving space is closed on all sides except for the insertion opening. The packaging device comprises an unfolding securing device for securing the packaging device in the insertion position against being completely unfolded back into the starting position.

In a second aspect of the present disclosure, a medical, in particular sterile, packaging system for sieve baskets comprises a plurality of medical packaging devices. At least one of the plurality of medical packaging devices is in the form of a medical packaging device for sterile packaging of a sieve basket. The packaging device defines a receiving space for accommodating a sieve basket in a packaging position and an insertion opening for inserting a sieve basket into the receiving space. The insertion opening is open in an insertion position. The packaging device is made from a flat material sheet that is unfolded in a starting position by folding multiple times. The receiving space in the insertion position has two abutting receiving space flat material sheet surface regions, which are delimited by at least three fold lines of the flat material sheet in such a way that the receiving space is closed on all sides except for the insertion opening. The packaging device comprises an unfolding securing device for securing the packaging device in the insertion position against being completely unfolded back into the starting position.

In a third aspect of the present disclosure, a method for producing a medical packaging device for sterile packaging of a sieve basket is provided. The packaging device is configured with a receiving space for accommodating a sieve basket in a packaging position and an insertion opening for inserting a sieve basket into the receiving space. The insertion opening is open in an insertion position. The packaging device is made from a flat material sheet that is unfolded in a starting position by folding multiple times. The receiving space in the insertion position has two abutting receiving space flat material sheet surface regions, which are delimited by at least three fold lines of the flat material sheet in such a way that the receiving space is closed on all sides except for the insertion opening. The packaging device is secured in the insertion position against being completely unfolded back into the starting position.

In a fourth aspect of the present disclosure, a method for sterile packaging of a sieve basket with a medical packaging device is provided, wherein a medical packaging device is provided. The packaging device defines a receiving space for accommodating a sieve basket in a packaging position and an insertion opening for inserting a sieve basket into the receiving space. The insertion opening is open in an insertion position. The packaging device is made from a flat material sheet that is unfolded in a starting position by folding multiple times. The receiving space in the insertion position has two abutting receiving space flat material sheet surface regions, which are delimited by at least three fold lines of the flat material sheet in such a way that the receiving space is closed on all sides except for the insertion opening. The packaging device comprises an unfolding securing device for securing the packaging device in the insertion position against being completely unfolded back into the starting position. The sieve basket is inserted through the insertion opening into the receiving space. The packaging device is transferred from the insertion position into a closed position in which the insertion opening is closed by folding a free end of the packaging device over the insertion opening.

BRIEF DESCRIPTION OF THE DRAWING FIGURES

The foregoing summary and the following description may be better understood in conjunction with the drawing figures, of which:

FIG. 11 shows a schematic depiction of the arrangement from FIG. 10 in the closed position before the activation of closure elements;

FIG. 12 shows a schematic perspective total view of the arrangement from FIG. 11 with activated closure elements;

FIG. 16 shows a schematic depiction of an embodiment of a medical packaging system.

DETAILED DESCRIPTION

Figure 1:
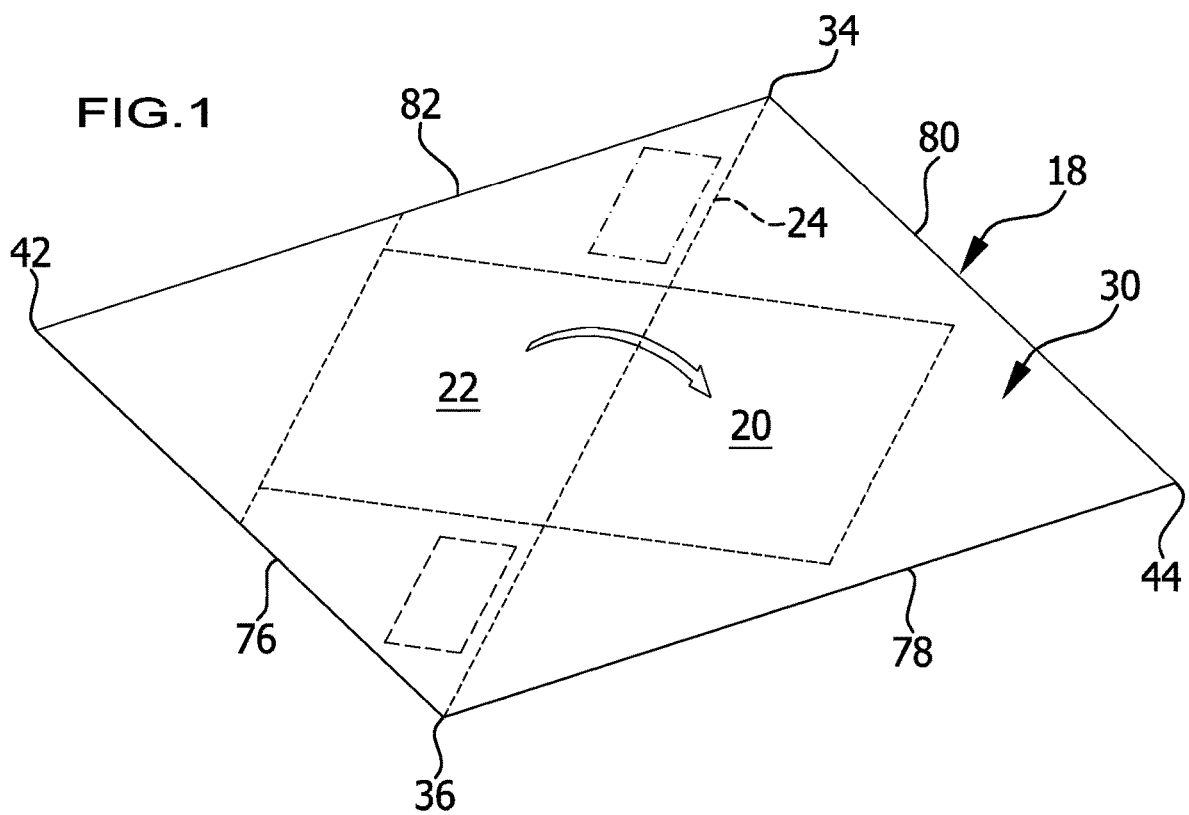
FIG. 1 shows a schematic perspective depiction of an embodiment of a flat material sheet for forming a packaging device in an unfolded starting position.

Although the present disclosure is illustrated and described herein with reference to specific embodiments, the present disclosure is not intended to be limited to the details shown. Rather, various modifications may be made in the details without departing from the present disclosure.

The present disclosure relates to a medical packaging device for sterile packaging of a sieve basket, wherein the packaging device defines a receiving space for accommodating a sieve basket in a packaging position and an insertion opening for inserting a sieve basket into the receiving space, wherein the insertion opening is open in an insertion position, wherein the packaging device is made from a flat material sheet that is unfolded in a starting position by folding multiple times, wherein the receiving space in the insertion position has two abutting receiving space flat material sheet surface regions, which are delimited by at least three fold lines of the flat material sheet in such a way that the receiving space is closed on all sides except for the insertion opening, wherein the packaging device comprises an unfolding securing device for securing the packaging device in the insertion position against being completely unfolded back into the starting position.

The proposed medical packaging device for sterile packaging of a sieve basket enables a user, in particular, to introduce, in particular slide, the sieve basket through the insertion opening into the receiving space. The medical packaging device provided in the insertion position then has the advantage, in particular, that a substantial portion of the folds of the flat material sheet that would otherwise would typically have to be performed by the user, as is stipulated by the DIN norm stated above, are no longer necessary. After inserting the sieve basket into the receiving space, the user must merely close the insertion opening, namely, for example, by folding a free end of the packaging device over the insertion opening. Furthermore, the unfolding securing device makes it possible to secure the medical packaging device in the insertion position. For example, folded over tabs or flaps of the packaging securing device can be secured by the unfolding securing device. It can thus be prevented, in particular, that the packaging device is able to be completely unfolded back into the starting position. The packaging device preassembled by folding is additionally secured by the unfolding securing device, thereby further improving a handling of the packaging device for sterile packaging of a sieve basket for a user. A securing can be effected, in particular, by adhesion with an adhesive, for example cyanoacrylates or hotmelt adhesives, by a double-sided adhesive tape, by ultrasonic welding, or by a bonded-on Velcro fastener.

It is favorable if the flat material sheet defines a first flat material side face and a second flat material side face, if the first flat material side face and the second flat material side face face in opposite directions in the starting position, and if the first flat material side face comprises the two receiving space flat material sheet surface regions. It can thus be ensured, in particular, that the sieve basket can only come into contact with one of the two flat material side faces of the flat material sheet, namely with the first flat material side face, when packaging with the packaging device. Contact and thus contamination of the sieve basket with the second flat material side face can thus be avoided.

It is advantageous if the packaging device in the insertion position comprises at least three fold lines. In particular, it may comprise three, four, five, six, or seven fold lines. The more fold lines the packaging device already comprises, the fewer folds a user still has to perform after they have introduced the sieve basket into the receiving space of the packaging device. The preassembled packaging device can thus have different levels of preassembly by way of the number of fold lines, depending on how much support a user requires in the packaging of sterile containers.

The packaging device can be configured in a simple manner if the flat material sheet is quadrangular in the starting position. In particular, it may be of rectangular configuration. The flat material sheet is preferably of square or substantially square configuration. The makes it possible, in particular, to produce defined fold lines in a simple manner, for example diagonal fold lines that connect opposing corners of the flat material sheet to one another.

It is favorable if one of the at least three fold lines is configured in the form of a main fold line and if the main fold line connects two main corners of the flat material sheet that are located opposite one another in the starting position. If the flat material sheet is square, it is divided by the main fold line into two identical triangles that lie on one another after a first fold.

The packaging device can be handled in a simple manner if the main fold line extends in parallel or substantially in parallel to the insertion opening.

It is favorable if two of the at least three fold lines are configured in the form of side fold lines running in parallel or substantially in parallel to one another and if the side fold lines extend transversely to the main fold line. In particular, the side fold lines may extend perpendicularly to the main fold line. The receiving space can thus be delimited by the main fold line and the two side fold lines. Distances of the two side fold lines thus also define, in particular, a size, for example a width, of the receiving space.

A distance of the two side fold lines from one another favorably corresponds at least to a third of the distance of the main corners from one another. It can thus be prevented, in particular, that the main corners protrude beyond the respective other side fold line and then have to be folded over again when folding the other main corner about the other side fold line. As a result of the proposed distance specification, in particular, a particularly flat packaging device in the insertion position can be provided.

The main corners are preferably positioned on the main fold line or substantially on the main fold line in the insertion position. The side fold lines can thus be configured perpendicularly to the main fold line in a simple manner.

It order to be able to set the receiving space in the desired manner, it is advantageous if the two receiving space flat material sheet surface regions are delimited by the main fold line.

In accordance with a further preferred embodiment of the present disclosure, provision may be made that the flat material sheet in the starting position comprises two opposing secondary corners, that the two secondary corners lie on one another in a first folded position in which the flat material sheet is folded from the starting position about the main fold line, that the packaging device comprises a first release tab, that the first release tab is formed by folding back a first one of the two secondary corners from the first folded position into a second folded position about a secondary fold line, and that the secondary fold line runs in parallel or substantially in parallel to the main fold line and extends between the main fold line and the secondary corners in the first folded position. This configuration makes it possible, in particular, to use one of the two secondary corners, in this case the first secondary corner, as part of a release tab. Using this first release tab, a user can release the packaging device from a sieve basket in a simple manner. They must merely grasp and pull the first release tab with the first secondary corner. They can thus unfold the packaging device from the sieve basket in a fast and secure manner.

The handling of the packaging device can be improved in a simple manner if the first release tab projects over the main fold line in the insertion position. Thus, for example, a lappet projects with the first secondary corner over the main fold line so that a user can grasp this lappet in order to quickly and securely open the packaging device.

A distance of the secondary fold line from the main fold line is favorably smaller than a distance from the secondary corners in the first folded position. As a result of this distance specification, it can be achieved, in particular, that the first release tab projects over the main fold line in the insertion position.

The secondary fold line preferably delimits the insertion opening. To insert the sieve basket, the secondary fold line merely must be raised slightly such that the two receiving space flat material sheet surface regions abutting against one another in the insertion position are moved slightly away from one another, such that the sieve basket can be slid into the receiving space in a simple and secure manner. The secondary fold line makes it easier for the user to insert the sieve basket into the receiving space because it visibly delimits the insertion opening.

It is favorable if the first one of the two main corners is folded from the second folded position about a first one of the two side fold lines in the direction toward a second one of the two main corners into a third folded position and if the second one of the two main corners is folded from the third folded position into a fourth folded position about a second one of the two side fold lines in the direction toward the first one of the two side fold lines. In particular, a rectangular receiving space for a sieve basket can be defined as a result of this design. Said sieve baskets are typically also rectangular, for example square. Furthermore, the receiving space is closed in a defined manner on the sides by the two side fold lines.

The packaging device can be configured in a simple and compact manner if the fourth folded position defines the insertion position.

It may further be advantageous if the packaging device comprises a second release tab, if the second release tab is formed by folding a second one of the two secondary corners, which in the insertion position points away from the insertion opening, from the fourth folded position into a fifth folded position about a release tab main fold line in the direction toward the main fold line and by folding back the second one of the two secondary corners from the fifth folded position into a sixth folded position about a release tab secondary fold line in a direction away from the main fold line. Thus, in particular, a second lappet that protrudes from the packaging device after insertion of the sterile container into the receiving space can be formed, said lappet comprising the second secondary corner. When the user grips this lappet, they can release, in particular unfold, the packaging device from the sieve basket in a simple and defined manner.

A distance of the release tab main fold line from the main fold line is preferably greater than a distance from the secondary corners in the first folded position. In particular, it is favorable if the distance of the release tab main fold line from the main fold line is more than twice as great as the distance of the release tab main fold line from the secondary corners in the first folded position. Thus, in particular, it can be ensured that the second secondary corner in the sixth folded position projects over the release tab main fold line and thus away from the packaging device as a whole.

It is advantageous if a distance of the release tab secondary fold line from the release tab main fold line is greater than a distance from the second secondary corner, in particular at least 30% greater. Thus, in particular, a sufficiently large lappet can be formed, which can function as a second release tab for a user in order to remove the packaging device from the sterilization sieve tray in a secure and defined manner.

It is advantageous if the release tab main fold line and the release tab secondary fold line run in parallel or substantially in parallel to one another. In particular, they may run in parallel to the main fold line. This configuration makes it possible, in particular, to form a rectangular or, after insertion of a sieve basket into the receiving space, cuboidal or substantially cuboidal packaging device.

The insertion opening is advantageously open in the sixth folded position. This makes it possible, in particular, to provide the packaging device as a preassembled packaging device in the sixth folded position. A user can then slide a sieve basket directly into said preassembled packaging device and then must only fold the end with the second secondary corner pointing away from the insertion opening over the insertion opening in order to completely enclose the sieve basket accommodated in the receiving space.

It is favorable if the unfolding securing device comprises at least one securing element for securing the packaging device in the insertion position. In particular, a plurality of securing elements may be provided, for example two, three, four, or more, in order to secure the preassembled packaging device in the insertion position against being unfolded.

It is advantageous if the packaging device defines at least one first securing surface region and at least one second securing surface region, if the first securing surface region and the second securing surface region are different from the two receiving space flat material sheet surface regions that abut against one another in the insertion position, if the first securing surface region and the second securing surface region abut against one another in the insertion position, and if the at least one securing element connects the at least one first securing surface region and the at least one second securing surface region to one another in a force-locking and/or materially bonded manner, in particular by adhesion and/or welding. It is thus possible in the described manner, in particular, to connect securing surface regions to one another in a defined manner. In particular, it is excluded that the securing surface regions are defined by the receiving space flat material sheet surface regions. It is thus prevented, in particular, that the receiving space is made smaller. Securing surface regions may be defined, in particular, by surface regions that come to lie on one another after folding along a fold line. When these surfaces are connected to one another by a securing element or by a plurality of securing elements, the packaging device, in particular, can no longer be transferred into the starting position on its own or unintentionally by unfolding.

In order to connect a wide variety of surfaces to one another after folding the flat material sheet in order to securing them to one another, it is advantageous if the at least one first securing surface region and the associated at least one second securing surface region are comprised by the same flat material side face or by different flat material side faces. For example, securing surface regions may be defined near the main corners on the same flat material side face, namely the second flat material side face.

The packaging device can be configured in a simple manner if the at least one securing element is formed by a welding point, by an adhesive, or by an adhesive element. In particular, the adhesive element may have two adhesive surfaces facing away from one another, wherein in the insertion position the one of the two adhesive surfaces abuts against the at least one first securing surface region and wherein the other one of the two adhesive surfaces abuts against the at least one second securing surface region. The adhesive element may thus be configured, e.g., in the form of a strip of double-sided adhesive tape.

For example, such an adhesive element may already be applied on the unfolded flat material sheet, i.e. in the starting position, at that point or position where it is later required in order to be connected to a second securing surface region.

It is favorable if the at least one securing element is positioned in a region of the packaging device in which at least two layers formed by folding the flat material sheet lie on one another in the insertion position. In particular, the at least one securing element may be positioned in regions in which three, four, five, six, or more layers of the flat material sheet lie on one another. The last flap about one of the two side fold lines is preferably fixed with a securing element, for example on the formed flap about the other one of the two side fold lines.

In accordance with a further preferred embodiment of the present disclosure, provision may be made that the packaging device comprises at least one closure element for closing the packaging device in a packaging position in which the insertion opening is closed by folding the second secondary corner about a closure fold line in the direction toward the first secondary corner. The flap of the packaging device that is formed by folding about the closure fold line can thus be fixed with the at least one closure element, such that it can no longer swing back again by itself.

The packaging device can be configured and handled in a simple manner if the at least one closure element is configured in the form of an adhesive strip. In particular, it may be an adhesive strip in the form of a Z-shaped adhesive strip that is folded back on itself. Such Z-shaped adhesive strips are folded in a Z-shape in a starting position and are thus shorted to about a third of their total length. A free end can be grasped by a user, such that the three layers of the Z-shaped adhesive strip folded back on itself can be unfolded. The other end of the adhesive strip is fixedly connected to the second flat material side face, such that the closure element cannot unintentionally detach from the packaging device. A closure element arranged in that way simplifies the handling, because a user does not have to tear off such an adhesive strip themselves, for example from a roll. The adhesive strip is pre-fabricated exactly in the length in which it is required.

The at least one closure element is favorably arranged or formed on the second flat material side face. This makes it possible, in particular, to provide a flat material sheet in the unfolded starting position, on which one or more closure elements are already arranged, for example adhesive strips in the form of Z-shaped adhesive strips. In particular, one or more securing elements, for example in the form of double-sided adhesive strips, may be arranged on the second flat material side face as described above, which then when transferring the flat material sheet from the starting position into the insertion position must merely be freed of, for example, a peelable protective film on one side in order to then connect two securing surface regions to one another in the described manner.

It is favorable if the at least one closure element defines a closure element longitudinal direction and if the closure element longitudinal direction runs in parallel or substantially in parallel to one of the two side fold lines or in parallel or substantially in parallel to the main fold line. If the closure element longitudinal direction runs in parallel to one of the two side fold lines, the closure element can directly fix the flap of the packaging device that is folded over the insertion opening against being folded back. An optional or additional fixing may be effected, in particular, if further closure elements are provided, the closure element longitudinal directions of which run in parallel or substantially in parallel to the main fold line.

It is advantageous if in the insertion position the at least one closure element extends up to the release tab main fold line or up to one of the two side fold lines and in the closure position the at least one closure element projects over the release tab main fold line or extends over one of the two side fold lines. This proposed further development makes it possible, in particular, to simply and securely fix a flap of the packaging device folded over the insertion opening by folding about the closure fold line.

The packaging device can be formed in a simple and cost-effective manner if the flat material sheet is made of a cloth, a non-woven fabric, in particular a non-woven plastic fabric, or a packaging paper, in particular a crepe paper.

It is advantageous for handling, in particular in a hospital, if the packaging device is configured in the form of a disposable product. Complex processing of the packaging device can thus be avoided. In particular, the packaging device can be removed from the sieve basket in a simple and fast manner by pulling open, for example unfolding.

The packaging device is advantageously configured to be sterilizable, in particular sterilizable with hot steam. This makes it possible, in particular, to sterilize the sieve basket accommodated in the receiving space of the packaging device together with its contents after transferring the packaging device from the insertion position into the packaging position, for example by means of a hot steam sterilization process.

In order to be able to ensure a secure packaging of a sterile container, it is advantageous if the packaging device is made of a one-piece, in particular monolithic, flat material sheet.

Further, the present disclosure relates to a medical, in particular sterile, packaging system for sieve baskets comprising a plurality of medical packaging devices, wherein at least one of the plurality of medical packaging devices is in the form of a medical packaging device for sterile packaging of a sieve basket, wherein the packaging device defines a receiving space for accommodating a sieve basket in a packaging position and an insertion opening for inserting a sieve basket into the receiving space, wherein the insertion opening is open in an insertion position, wherein the packaging device is made from a flat material sheet that is unfolded in a starting position by folding multiple times, wherein the receiving space in the insertion position has two abutting receiving space flat material sheet surface regions, which are delimited by at least three fold lines of the flat material sheet in such a way that the receiving space is closed on all sides except for the insertion opening, wherein the packaging device comprises an unfolding securing device for securing the packaging device in the insertion position against being completely unfolded back into the starting position.

Thus, in particular, a plurality of such packaging devices can be provided, into which a user must then insert sieve baskets already loaded with instruments or implants in order to package same.

It is favorable if at least two of the plurality of medical packaging devices differ from one another in shape and/or size and/or in the material of which the flat material sheet is made. Thus, in particular, preassembled packaging devices of different sizes can be provided in order to be able to quickly and simply package sterilization sieve trays of different sizes and shapes in the manner described above.

It is advantageous if the packaging system comprises an outside packaging for the plurality of packaging devices. In particular, the outside packaging may be configured in the form of a dispenser device with a removal opening through which the packaging devices are individually removable from the dispenser device. For example, dispenser devices of that kind can be provided in a processing unit for medical products, formerly also referred to as Central Sterile Supply Department. For packaging a sterilization sieve tray, a user then removes the packaging device suited to the respective shape and size of the sterilization sieve tray from a provided dispenser device and then slides the sterilization sieve tray into the receiving space of the packaging device. The complex wrapping up of the sterilization sieve tray in a flat material sheet that has been required until now is no longer necessary. The processing of goods to be sterilized before sterilization can then take place significantly faster.

The packaging system preferably comprises at least one sieve basket. In particular, instruments or implants that must be provided under sterile conditions for a medical, in particular surgical, procedure can be placed in the sieve basket.

Further, the present disclosure relates to a method for producing a medical packaging device for sterile packaging of a sieve basket, wherein the packaging device is configured with a receiving space for accommodating a sieve basket in a packaging position and an insertion opening for inserting a sieve basket into the receiving space, wherein the insertion opening is open in an insertion position, wherein the packaging device is made from a flat material sheet that is unfolded in a starting position by folding multiple times, wherein the receiving space in the insertion position has two abutting receiving space flat material sheet surface regions, which are delimited by at least three fold lines of the flat material sheet in such a way that the receiving space is closed on all sides except for the insertion opening, wherein the packaging device is secured in the insertion position against being completely unfolded back into the starting position.

As already described above, it is thereby prevented that the packaging device is able to unfold by itself in an undesired manner. This facilitates, in particular, the insertion of the sieve basket into the receiving space. By securing in the described manner, the packaging device can be provided with a dimensional stability that is advantageous for its handling.

It is favorable if the flat material sheet defines a first flat material side face and a second flat material side face, if the first flat material side face and the second flat material side face in the starting position face in opposite directions, and if the two receiving space flat material sheet surface regions are formed from the first flat material side face by folding the flat material sheet. Therefore, by folding the flat material sheet, two receiving space flat material sheet surface regions come into abutment against one another, which both form sections of the first flat material side face. It can thus be achieved that the receiving space is delimited only by surface regions of the first flat material side face.

The packaging device can be formed in a simple manner by folding the flat material sheet along at least three fold lines, in particular along three, four, five, six, or seven fold lines. This design makes it possible, in particular, to form the packaging device from one single, i.e. a one-piece, monolithic flat material sheet.

The packaging device can be produced in a simple manner if a flat material sheet is provided, which is quadrangular, in particular rectangular, in the starting position. Furthermore, it may optionally be of square or substantially square configuration. Flat material sheets of that kind can be produced and folded in a simple manner.

It is advantageous if one of the at least three fold lines is configured in the form of a main fold line, which connects two main corners of the flat material sheet that are located opposite one another in the starting position. Thus, for example, a square flat material sheet can be halved by the main fold line.

In order to be able to form the insertion opening in a defined manner, it is advantageous if it is configured extending in parallel or substantially in parallel to the main fold line.

It is further favorable if two of the at least three fold lines are configured in the form of side fold lines running in parallel or substantially in parallel to one another, which side fold lines extend transversely to the main fold line. Thus, in particular, the receiving space can be delimited and closed on three sides by the main fold line and the two side fold lines.

The two side fold lines are advantageously formed at a distance from one another, which corresponds at least to a third of a distance of the main corners from one another. It can thus be prevented, in particular, that the main corners have to be folded over multiple times, which would lead to regions forming in which many layers of the flat material sheet would lie on one another.

The packaging device can be formed in a simple and defined manner if the main corners are positioned on the main fold line or substantially on the main fold line by folding. Because the main corners are already located on the main fold line before folding about the side fold lines, said main fold line being defined as such, the side fold lines automatically run perpendicularly to the main fold line.

The receiving space can be predetermined in a defined manner if the two receiving space flat material sheet surface regions are delimited by the main fold line. Furthermore, they may also be delimited by the two side fold lines.

In accordance with a further preferred embodiment of the present disclosure, the flat material sheet in the starting position comprises two opposing secondary corners, that the two secondary corners are brought into a first folded position by folding the flat material sheet from the starting position about the main fold line, in which first folded position they lie on one another, that a first release tab of the packaging device is formed by folding back a first one of the two secondary corners about a secondary fold line from the first folded position into a second folded position, and that the secondary fold line runs in parallel or substantially in parallel to the main fold line and extends between the main fold line and the secondary corners in the first folded position. Thus, in particular, a release tab can be formed, which projects over the main fold line so that a user is able to securely grasp it, for example in order to unpack a sterile container accommodated in the receiving space of the packaging device.

The first release tab is favorably configured projecting over the main fold line in the insertion position. As already mentioned, a user can thus remove the packaging device from the sieve basket in a simple and secure manner.

It is advantageous if the secondary fold line is configured at a distance from the main fold line that is smaller than from the secondary corners in the first folded position. As a result of this distance specification, it can be ensured, in particular, that the first release tab projects over the main fold line in the insertion position.

It is favorable if the secondary fold line is configured delimiting the insertion opening. A user can thus, in particular, always immediately recognize where the insertion opening is. This facilitates, in particular, the insertion of a sieve basket into the receiving space of the packaging device.

It is advantageous if a first one of the two main corners is folded from the second folded position about a first one of the two side fold lines in the direction toward a second one of the two main corners into a third folded position and if the second main corner is folded from the third folded position into a fourth folded position about a second one of the two side fold lines in the direction toward the first side fold line. The receiving space can be delimited in a defined manner on three sides by these two folds. In particular, the folded over main corners may be secured, in particular in a force-locking and/or materially bonded manner, to that surface on which they rest after being folded over.

The packaging device is favorably configured in such a way that the fourth folded position defines the insertion position. Thus, only four folds are required to preassemble the packaging device such that it assumes the insertion position in which a sieve basket can be introduced into the receiving space in a simple and secure manner.

It is advantageous if a second release tab of the packaging device is formed by folding over a second one of the two secondary corners, which points away from the insertion opening in the insertion position, from the fourth folded position into a fifth folded position about a release tab main fold line in the direction toward the main fold line and by folding back the second secondary corner from the fifth folded position into a sixth folded position about a release tab secondary fold line in a direction away from the main fold line. This design enables a user, in particular, to grasp the packaging device not only on the first release tab, but also on the second release tab in order to remove it from the sieve basket.

It is favorable if the release tab main fold line is configured at a distance from the main fold line that is greater than from the secondary corners in the first folded position, in particular more than twice as great. As a result of this distance specification, it can be ensured, in particular, that the second secondary corner projects over the release tab main fold line and thus can be securely gripped by a user in a defined manner.

It is advantageous if the second release tab is configured in such a way that a distance of the release tab secondary fold line from the release tab main fold line is greater than a distance from the second secondary corner, in particular at least 30% greater. As a result of this distance specification, it can be ensured, in particular, that the second release tab has a sufficient size so that a user can securely grasp it in order to remove the packaging device from a sieve basket.

The method can be performed in a simple manner if the release tab main fold line and the release tab secondary line are configured running in parallel or substantially in parallel to one another. In particular, they may be configured in parallel to the main fold line.

The packaging device is preferably configured in such a way that the insertion opening is open in the sixth folded position. This has the advantage, in particular, that a user is also provided with the second release tab already preassembled and then does not have to form this release tab themselves by means of the described folds about the release tab main fold line and the release tab secondary fold line.

In order to prevent the packaging device from being able to unfold in an undesired manner from the insertion position back into the starting position of the flat material sheet, it is advantageous if the packaging device is secured in the insertion position with at least one securing element. For example, regions of the flat material sheet lying on one another by folding can thus be fixed to one another in order to give the packaging device a dimensional stability that is advantageous for good handleability.

It is favorable if the packaging device defines at least one first securing surface region and at least one second securing surface region, if the first securing surface region and the second securing surface region are different from the two receiving space flat material sheet surface regions that abut against one another in the insertion position, if the first securing surface region and the second securing surface region abut against one another in the insertion position, and if the at least one securing element connects the at least one first securing surface region and the at least one second securing surface region to one another in a force-locking and/or materially bonded manner, in particular by adhesion and/or welding. The two securing surface regions may define, in particular, abutting surface regions of the flat material sheet, which abut against one another after folding same about one of the fold lines. A folding back can thus be prevented when they are connected to one another, for example by adhesion and/or welding. In particular, an adhesive or a double-sided adhesive strip may be used here. If the flat material sheet is made of a plastic, the securing surface regions may, in particular, also be materially bonded to one another by ultrasonic welding.

It is advantageous if the packaging device is configured in such a way that the at least one first securing surface region and the associated at least one second securing surface region are comprised by the same flat material side face or by different flat material side faces. In particular, it is possible that only securing surface regions that are comprised by the second flat material side face, i.e. that flat material side face that does not delimit the receiving space, are connected to one another. It can thus be prevented, in particular, that the two receiving space flat material sheet surface regions are connected to one another, whereby the receiving space could be made smaller or entirely destroyed.

The packaging device can be configured in a simple manner if the at least one securing element is formed by a welding point, by an adhesive, or by an adhesive element. In particular, the adhesive element may have two adhesive surfaces facing away from one another and be attached in such a way, in particular in the starting position of the flat material sheet, that in the insertion position the one of the two adhesive surfaces abuts against the at least one first securing surface region and that the other one of the two adhesive surfaces abuts against the at least one second securing surface region. In particular when the adhesive element, which is configured as a double-sided adhesive strip, is already attached to the flat material sheet in the starting position on one of the securing surface regions, when producing the packaging device, for example, only a protective film must be peeled off the adhesive element in order to connect same to a further side surface region and thus to secure the packaging device in the insertion position.

In order to give the packaging device in the insertion position a high dimensional stability, it is advantageous if the at least one securing element is positioned in a region of the packaging device in which at least two layers formed by folding the flat material sheet lie on one another in the insertion position.

In accordance with a further preferred embodiment of the present disclosure, provision may be made that the packaging device is configured with at least one closure element for closing the packaging device in a packaging position in which the insertion opening is closed by folding the second secondary corner about a closure fold line in the direction toward the first secondary corner. Providing such a closure element makes it easier for a user to package a sieve basket, because they do not have to separately tear off such a closure element, for example from a roll of adhesive tape. The closure element is already positioned where it is required and ideally is also appropriately dimensioned.

It is favorable for the handling of the packaging device if the at least one closure element is configured in the form of an adhesive strip. In particular, it may be configured in the form of an adhesive strip that is folded back on itself in a Z-shaped manner.

The at least one closure element is preferably arranged or formed on the second flat material side face. In particular, it may already be arranged or formed there in the starting position of the flat material sheet. In particular, it is possible to arrange or to fix all closure elements and all securing elements on the flat material sheet already in the starting position. This simplifies the production of the packaging device, because the flat material sheet can already be pre-assembled in the described manner with securing and closure elements. It then merely has to be transferred from the starting position into the insertion position by means of a plurality of folds.

The at least one closure element favorably defines a closure element longitudinal direction and is arranged on the packaging device in such a way that the closure element longitudinal direction runs in parallel or substantially in parallel to one of the two side fold lines or in parallel or substantially in parallel to the main fold line. Thus, in particular, a flap folded over the insertion opening can be quickly and securely fixed to the second secondary corner, namely, for example, in a direction transverse, in particular perpendicular, to the insertion opening if it runs in parallel to the main fold line, or transversely to this direction.

It is favorable if the at least one closure element is arranged in such a way that in the insertion position it extends up to the release tab main fold line or up to one of the two side fold lines and in the closure position extends over the release tab main fold line or over one of the two side fold lines. The closed position is defined, in particular, as that position in which the insertion opening is closed. The closure element must then merely be guided across the release tab main fold line or across the respective side fold line in order to laterally fix the flap of the flat material sheet closing the insertion opening.

The packaging device can be produced in a simple manner if the flat material sheet is made of a cloth, a non-woven fabric, in particular a non-woven plastic fabric, or a packaging paper, in particular a crepe paper.

Sieve baskets can be packaged in a sterile manner if the packaging device is configured in the form of a disposable product. In particular, the packaging device may be made of a sterile flat material sheet.

So that the sterilization sieve tray that is packaged with a packaging device can be sterilized, it is favorable if the packaging device is configured to be sterilizable, in particular sterilizable with hot steam. Appropriate materials may be selected from which the flat material sheet can be made.

In particular, in order to avoid undesired opening of the packaging device, it is advantageous if the packaging device is made of a one-piece, in particular monolithic, flat material sheet.

Further, the present disclosure relates to a method for sterile packaging of a sieve basket with a medical packaging device, wherein a medical packaging device is provided, wherein the packaging device defines a receiving space for accommodating a sieve basket in a packaging position and an insertion opening for inserting a sieve basket into the receiving space, wherein the insertion opening is open in an insertion position, wherein the packaging device is made from a flat material sheet that is unfolded in a starting position by folding multiple times, wherein the receiving space in the insertion position has two abutting receiving space flat material sheet surface regions, which are delimited by at least three fold lines of the flat material sheet in such a way that the receiving space is closed on all sides except for the insertion opening, wherein the packaging device comprises an unfolding securing device for securing the packaging device in the insertion position against being completely unfolded back into the starting position, wherein the sieve basket is inserted through the insertion opening into the receiving space, and wherein the packaging device is transferred from the insertion position into a closed position in which the insertion opening is closed by folding a free end of the packaging device over the insertion opening.

It is thus possible in the manner already described at the outset to package a sieve basket significantly faster. In particular, the flat material sheet no longer has to be complexly folded by a user around the sieve basket, which causes a high time and thus cost expenditure. The sieve basket must merely be slid through the insertion opening into the receiving space. The insertion opening is closed by folding a free end of the packaging device over same. The sieve basket is then optimally packaged. In particular, this method can be performed by users that are not extensively trained.

The folded over free end is preferably fixed in the closed position with at least one closure element. In particular, two, three, four, or even more closure elements may be provided in order to fix the folded over free end in the closed position. A sieve basket is thus securely packaged. The packaging device cannot release from the sieve basket in an unintentional manner.

Figure 7:
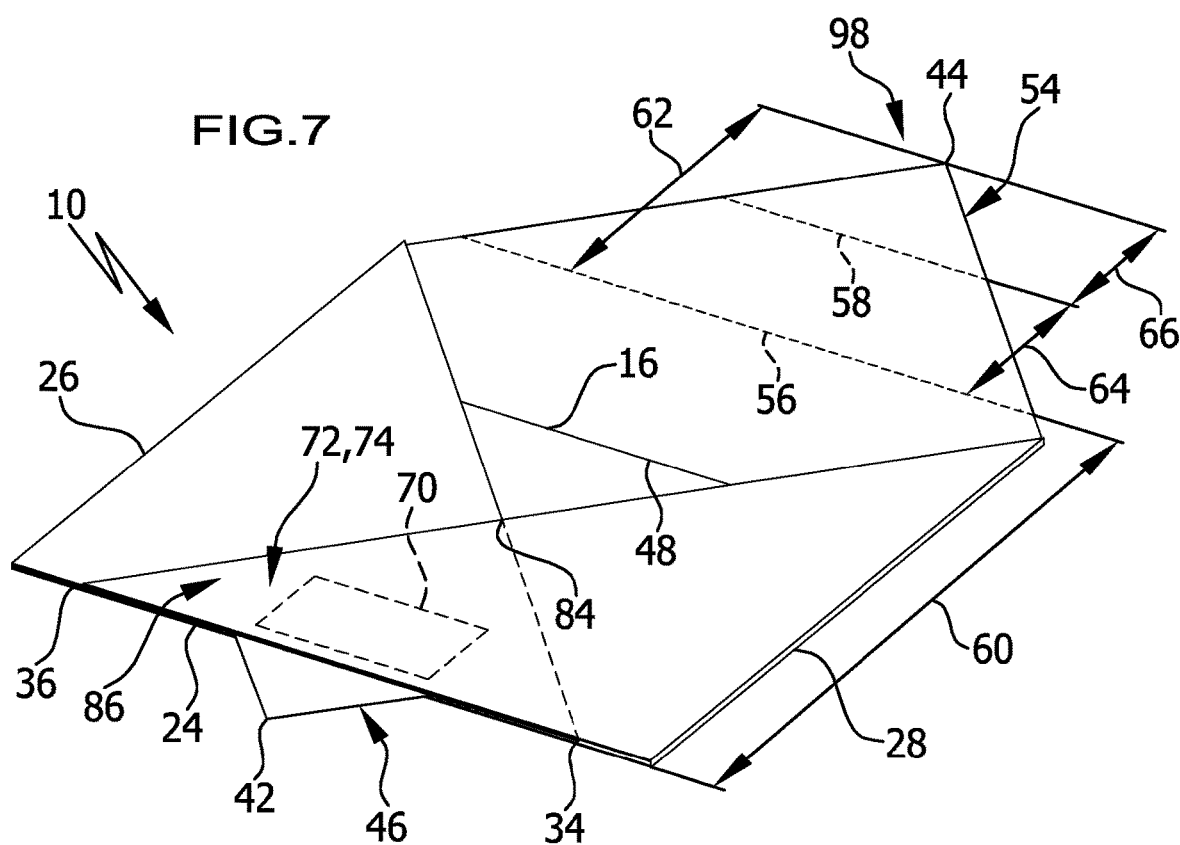
FIG. 7 shows a schematic depiction of the flat material sheet in the fourth folded position, which defines an insertion position.
Figure 8:
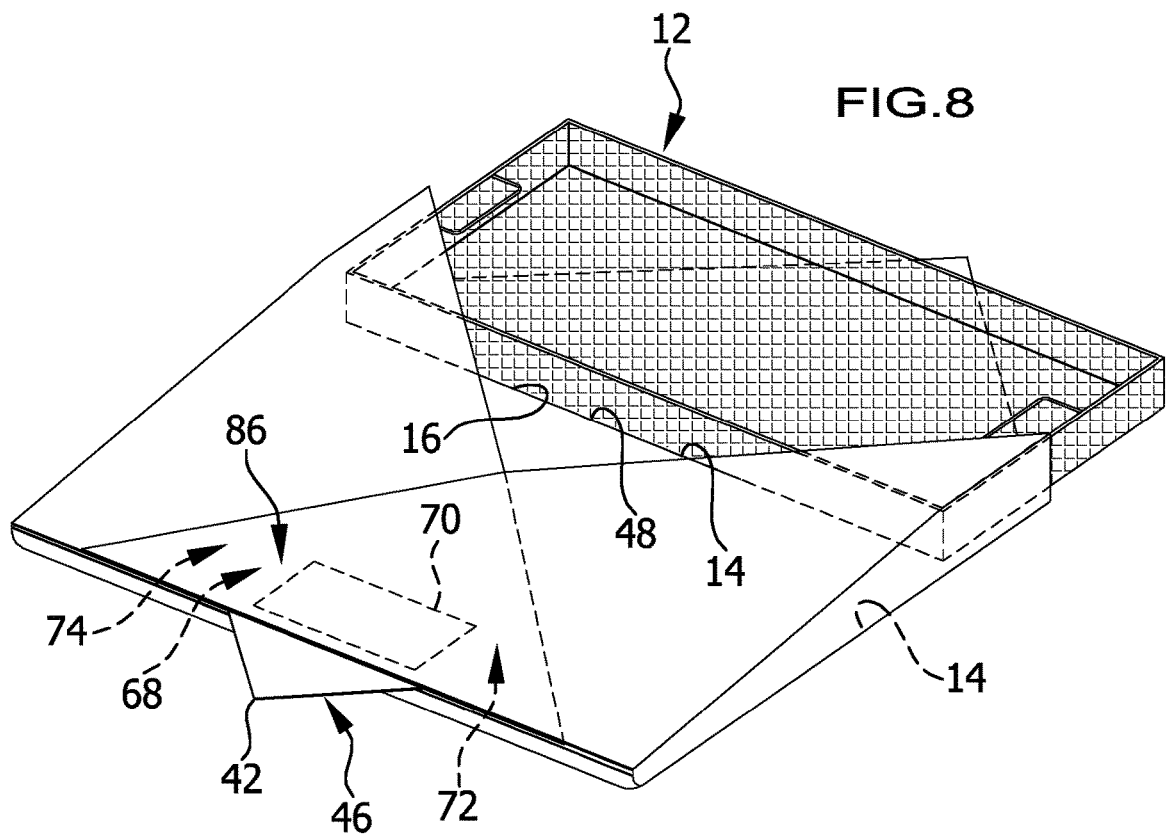
FIG. 8 shows a schematic depiction of the arrangement from FIG. 7 upon insertion of a sieve basket through an insertion opening of the packaging device into a receiving space thereof.

Schematically depicted in FIG. 7 and denoted as a whole with the reference numeral 10 is an embodiment of a medical packaging device. It serves for the sterile packaging of a sieve basket 12, which is schematically depicted in FIG. 8. In FIG. 8, instruments or implants that are normally introduced into the sieve basket 12 are not depicted for the sake of clarity.

The packaging device 10 defines a receiving space 14 for accommodating the sieve basket 12 in a packaging position.

The packaging device 10 further defines an insertion opening 16 through which the sieve basket 12 can be introduced into the receiving space 14.

The insertion opening 16 is open in the insertion position of the packaging device depicted in FIG. 8.

Figure 15:
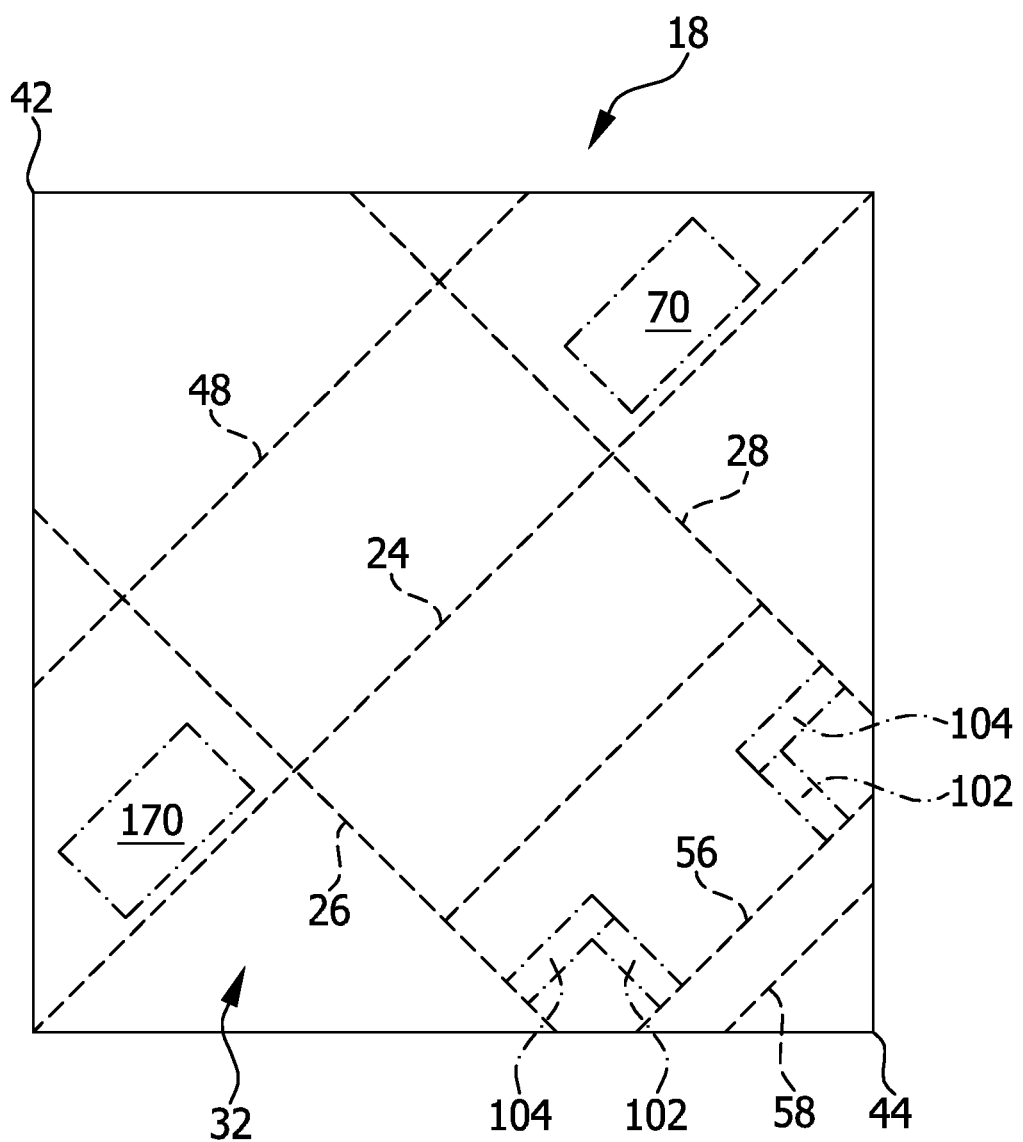
FIG. 15 shows a schematic depiction of a plan view of a second flat material side face of a flat material sheet.

The packaging device 10 is made from a flat material sheet 18. Such a flat material 10 sheet 18 is schematically depicted in FIG. 1. FIG. 15 also schematically shows a flat material sheet 18. The packaging device 10 is formed from the flat material sheet 18 by folding multiple times, as is described in detail in the following.

Figure 2:
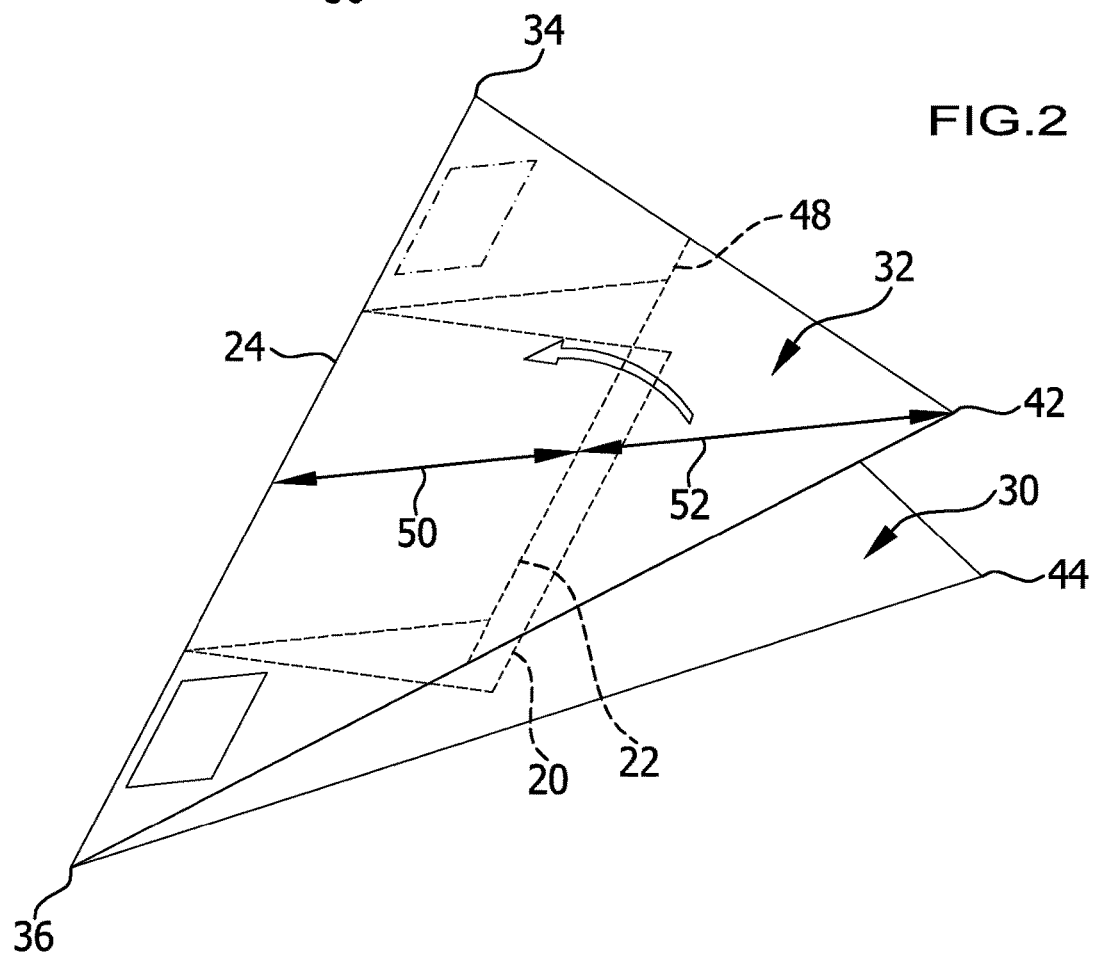
FIG. 2 shows a schematic depiction of the flat material sheet from FIG. 1 in a first folded position.
Figure 3:
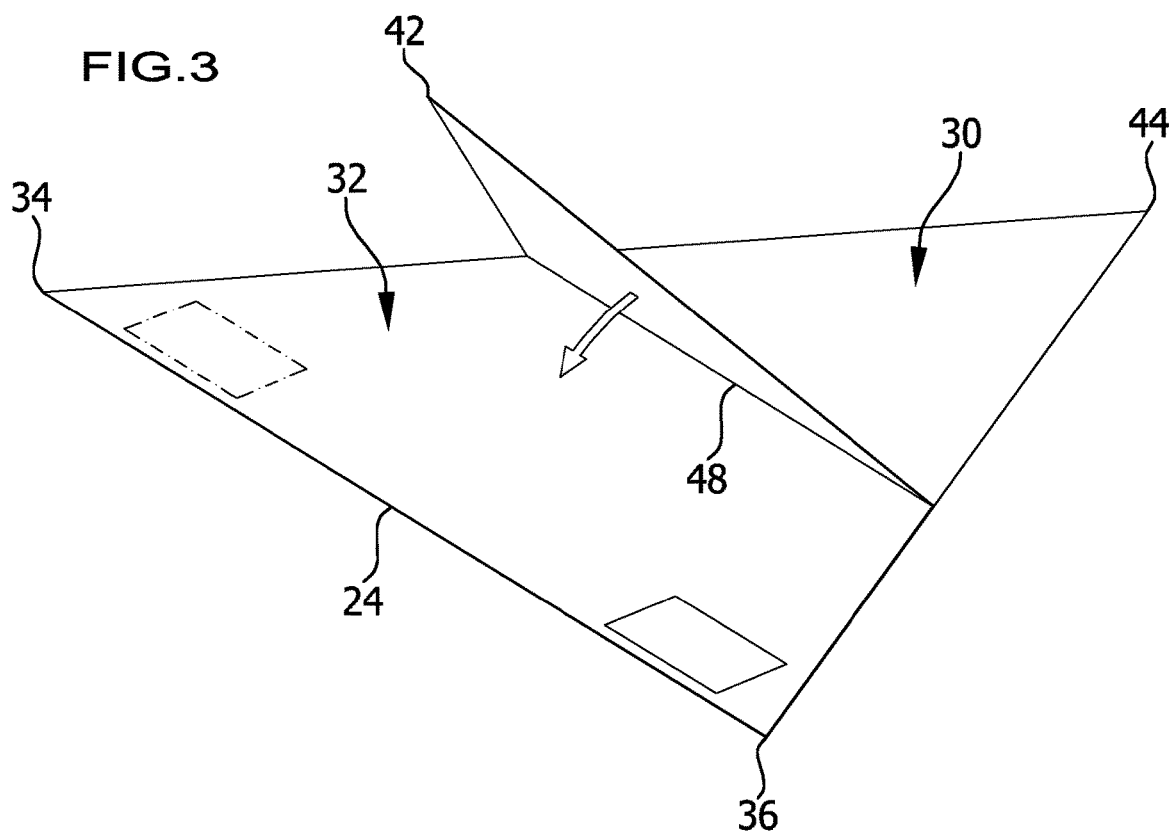
FIG. 3 shows a schematic perspective view of the flat material sheet upon transferring from the first folded position into a second folded position.

In the insertion position, the receiving space 14 has two abutting receiving space flat material sheet surface regions, namely a first receiving space flat material sheet surface region 20 and a second receiving space flat material sheet surface region 22 of identical size, which are schematically shown in FIGS. 1 and 2.

The two receiving space flat material sheet surface regions 20 and 22 are delimited by three fold lines of the flat material sheet 18, namely a main fold line 24 and two side fold lines, namely a first side fold line 26 and a second side fold line 28. The main fold line 24 and the side fold lines 26 and 28 delimit the receiving space 14 in such a way that it is closed on all sides except for the insertion opening 16.

The flat material sheet 18 defines a first flat material side face 30 and a second flat material side face 32, which in the starting position of the unfolded flat material sheet 18 face in opposite directions. As is schematically shown with dashed lines in FIG. 1, the first flat material side face 30 comprises the two receiving space flat material sheet surface regions 20 and 22. FIG. 15 shows a plan view of the flat material side face 32.

The flat material sheet 18 in the starting position is quadrangular, namely square, as schematically depicted in the embodiment in FIG. 1. One of the three stated fold lines is configured in the form of a main fold line 24, which connects two main corners 34 and 36 of the flat material sheet 18 to one another, which are located opposite one another in the starting position, namely a first main corner 34 and a second main corner 36.

The main fold line 24 extends in parallel to the insertion opening 16. The side fold lines 28 and 30 run in parallel to one another and extend transversely to the main fold line 24, namely perpendicularly thereto. A distance 38 of the two side fold lines 28 and 30 from one another corresponds at least to a third of a distance 40 of the two main corners 34 and 36 from one another.

As schematically depicted in FIG. 7, the main corners 34 and 36 are positioned on the main fold line 24 in the insertion position.

The main fold line 24 further delimits the two receiving space flat material sheet surface regions 20 and 22, as is schematically depicted in FIG. 1.

In the starting position, the flat material sheet 18 defines two opposing secondary corners, namely a first secondary corner 42 and a second secondary corner 44.

The two secondary corners 42 and 44 lie on one another in a first folded position, as it is schematically depicted in FIG. 2, in which the flat material sheet 18 is folded from the starting position about the main fold line 24.

The packaging device 10 comprises a first release tab 46, which is formed by folding back the first secondary corner 42 from the first folded position into a second folded position about a secondary fold line 48. The secondary fold line 48 runs in parallel to the main fold line 24. It extends between the main fold line 24 and the secondary corners 42 and 44 in the first folded position.

As can be easily seen, in particular, in FIGS. 4 to 12, the first release tab 46, which is configured in the form of a triangular lappet with the first secondary corner 42, projects over the main fold line 24 in the insertion position.

A distance 50 of the secondary fold line 48 from the main fold line 24 is smaller than a distance 52 from the secondary corners 42 or 44 in the first folded position, as is schematically depicted in FIG. 2.

As can be easily seen, in particular, in FIGS. 7 and 8, the secondary fold line 48 delimits the insertion opening 16.

Figure 4:
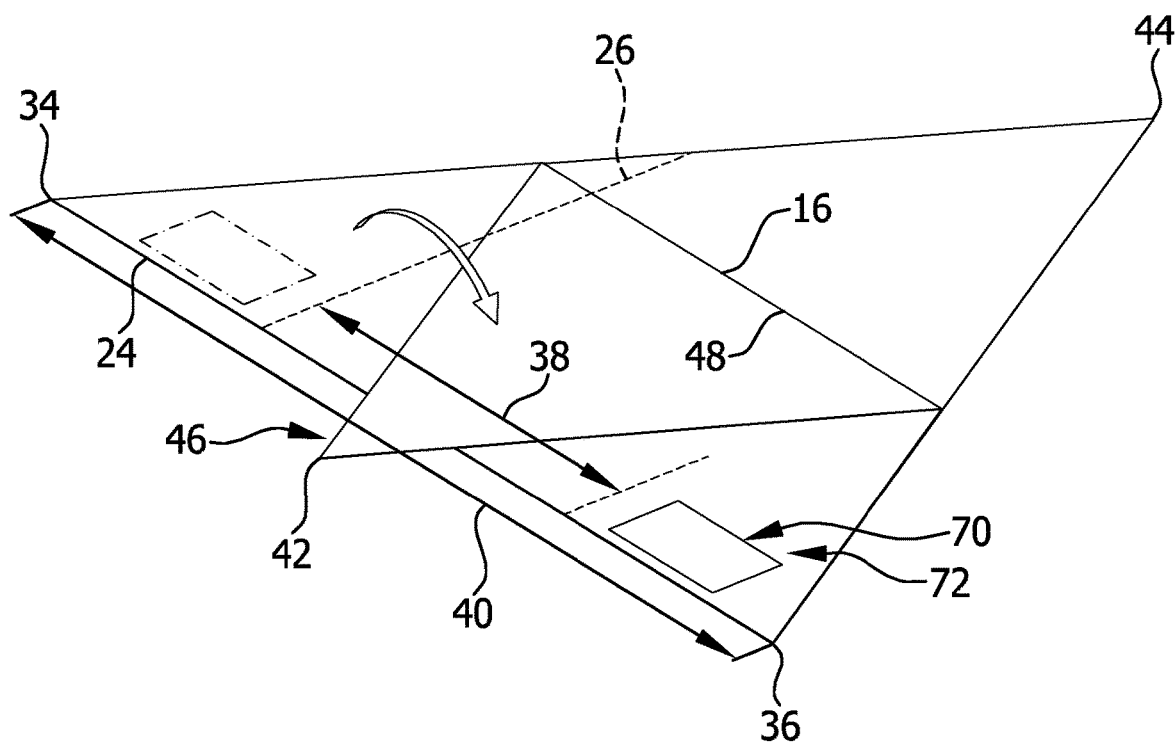
FIG. 4 shows a schematic perspective arrangement of the flat material sheet in the second folded position.
Figure 5:
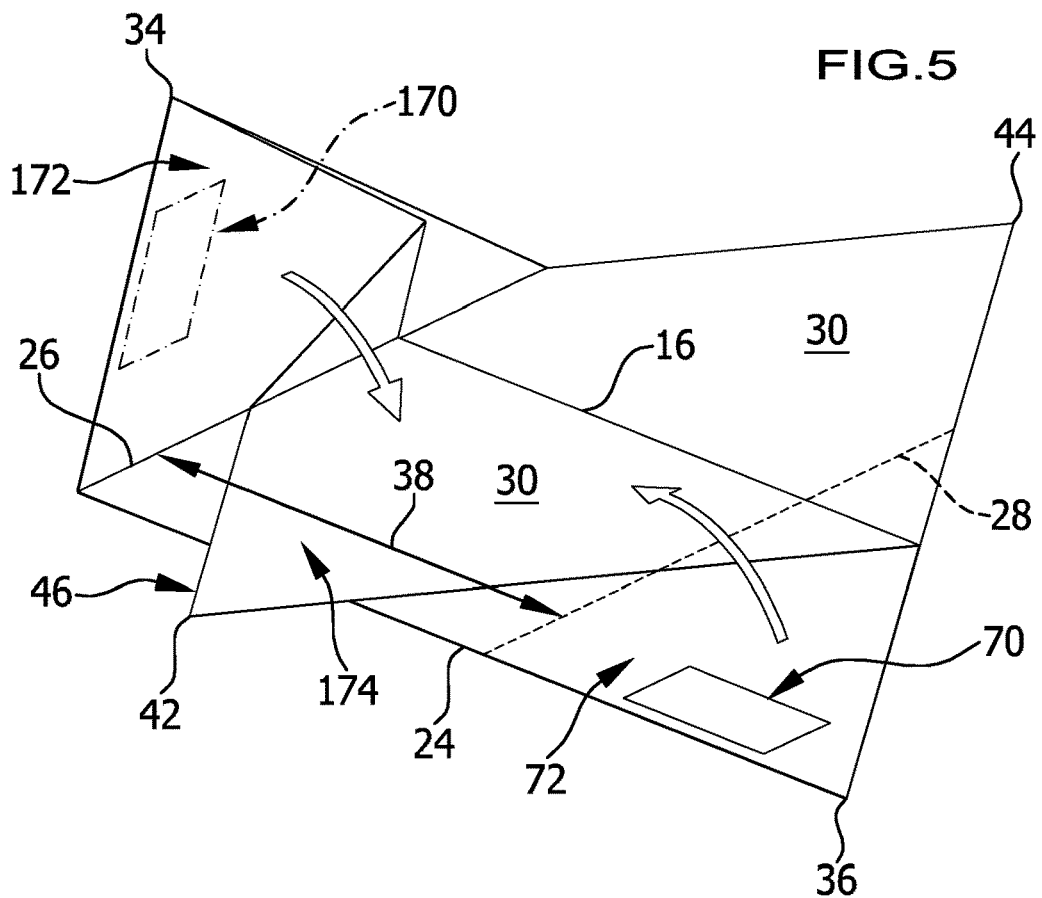
FIG. 5 shows a schematic perspective view of the flat material sheet from FIG. 4 upon transferring from the second folded position into a third folded position.
Figure 6:
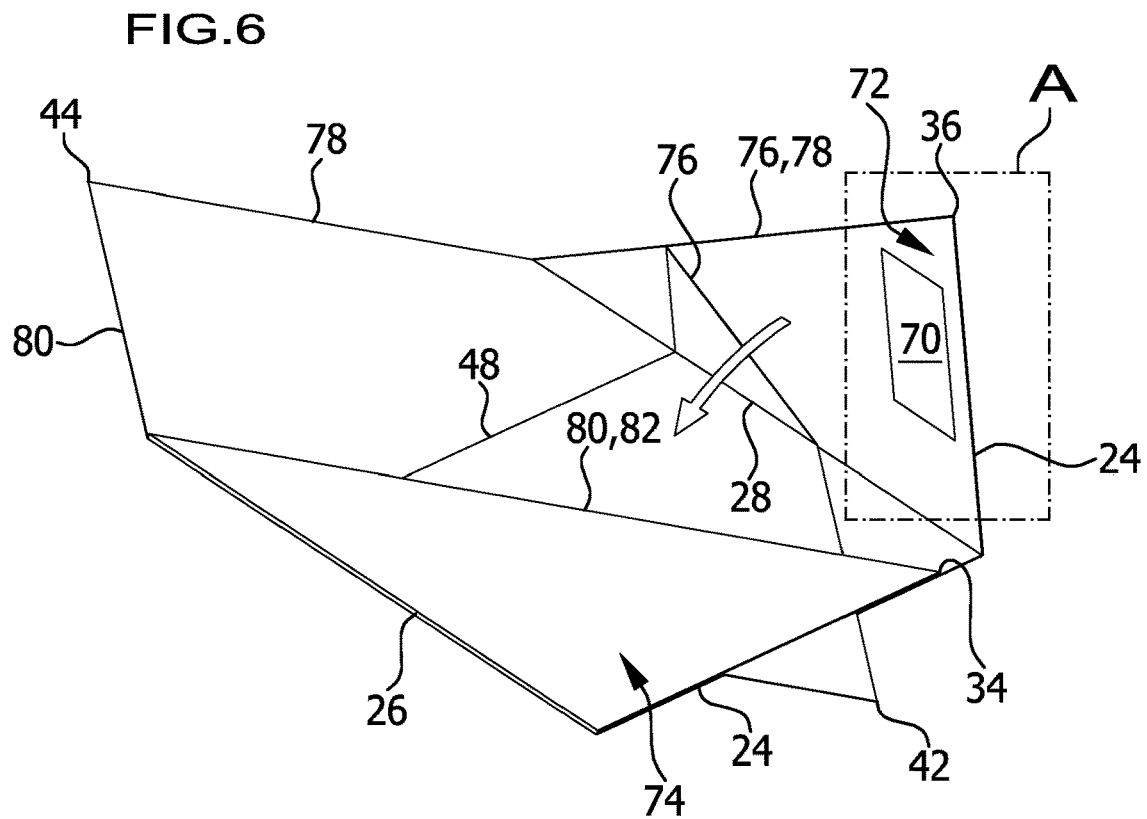
FIG. 6 shows a schematic perspective view of the flat material sheet from FIG. 5 upon transferring from the third folded position into a fourth folded position.

The second folded position is schematically depicted in FIG. 4. Commencing from the second folded position, the first main corner 34 is folded about the first side fold line 26 in the direction toward the second main corner 36 into a third folded position, as is schematically depicted in FIG. 6. The folding operation is schematically depicted in FIG. 5.

The second main corner 36 is transferred from the third folded position into a fourth folded position that is schematically depicted in FIG. 7, namely by folding about the second side fold line 28 in the direction toward the first side fold line 26. As already mentioned above, the fourth folded position defines the insertion position in which the sieve basket 12 can be introduced through the insertion opening 16 into the receiving space 14.

The packaging device 10 further comprises a second release tab 54. The second release tab 54 is formed by folding the second secondary corner 44, which points away from the insertion opening 16 in the insertion position, from the fourth folded position into a fifth folded position about a release tab main fold line 56 in the direction toward the main fold line 24. Furthermore, the second secondary corner 44 is folded from the fifth folded position into a sixth folded position about a release tab secondary fold line 58 back in a direction away from the main fold line 24.

Figure 9:
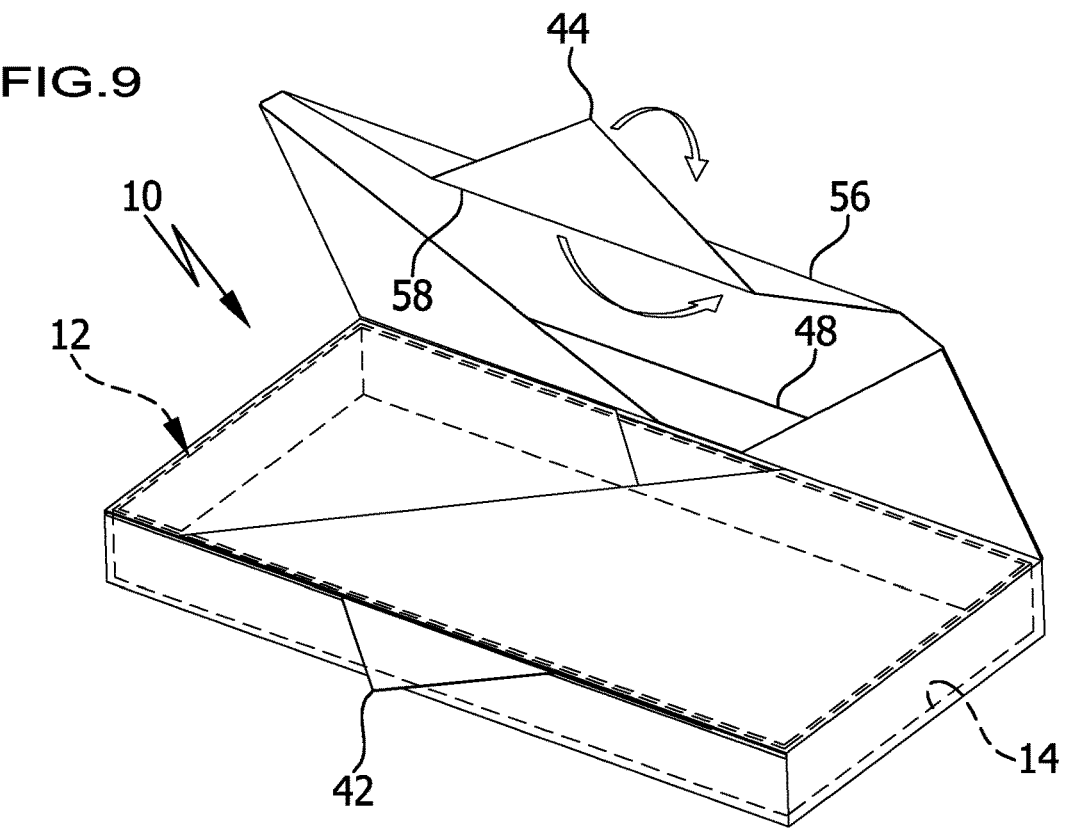
FIG. 9 shows a schematic depiction of the arrangement from FIG. 8 upon transferring from the fourth folded position into a fifth folded position and into a sixth folded position.
Figure 10:
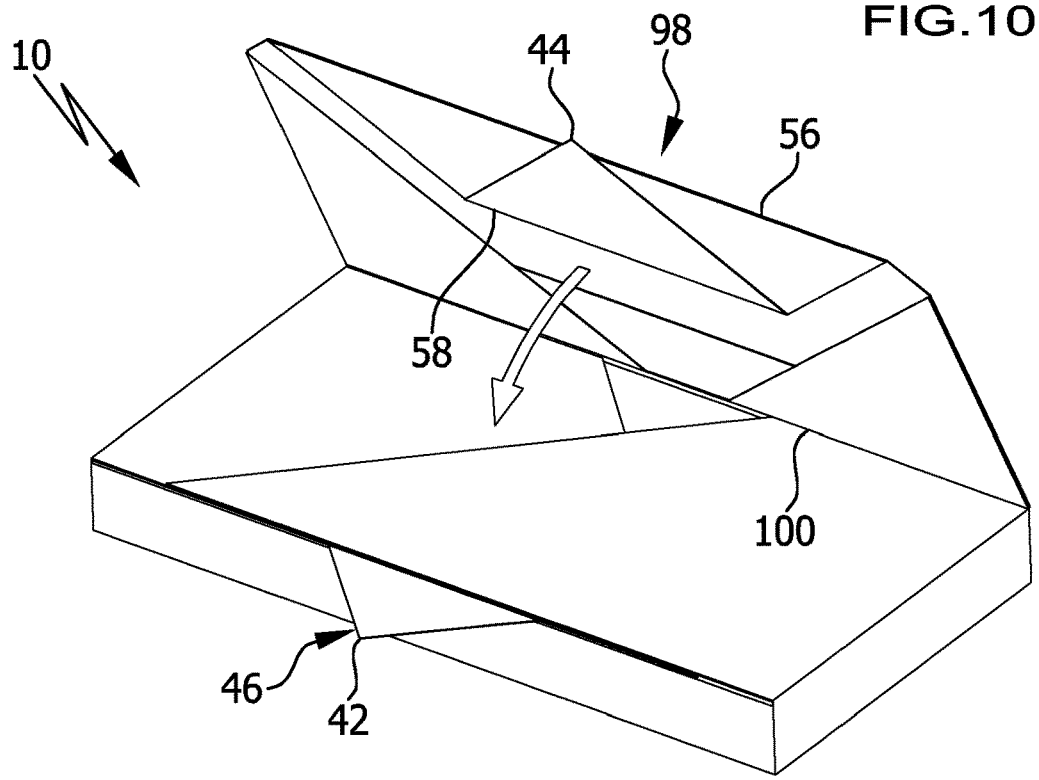
FIG. 10 shows a schematic depiction of the arrangement from FIG. 9 upon transferring from the sixth folded position into a closed position.

As can be seen, in particular, in FIGS. 9 and 10, the insertion opening 16 is also open in the sixth folded position, i.e., when the second release tab 54 is formed. Therefore, the sixth folded position also defines an insertion position of the packaging device 10.

A distance 60 of the release tab main fold line 56 from the main fold line 24 is, as schematically depicted in FIG. 7, greater than a distance 62 from the secondary corners 42 or 44 in the first folded position. In the embodiment depicted in the Figures, the distance 60 is more than twice as great as the distance 62.

Furthermore, a distance 64 of the release tab secondary fold line 58 from the release tab main fold line 56 is greater than a distance 66 from the second secondary corner 44.

The packaging device 10 further comprises an unfolding securing device 68 for securing the packaging device 10, in particular a dimensional stability thereof, in the insertion position, namely against being completely unfolded back into the starting position.

The release tab main fold line 56 and the release tab secondary fold line 58 run in parallel to one another and in parallel to the main fold line 24.

The unfolding securing device 68 comprises a first securing element 70 for securing the packaging device 10 in the insertion position.

The packaging device 10 comprises at least one first securing surface region 72 and a second securing surface region 74. These are surface regions of the flat material sheet 18, which are different from the receiving space flat material sheet surface regions 20 and 22.

The first securing surface region 72 and the second securing surface region 74 abut against one another in the insertion position. The securing element 70 connects the two securing surface regions 72 and 74 to one another in a force-locking and/or materially bonded manner.

In the embodiment depicted in the Figures, the second flat material side face 32 comprises both securing surface regions 72 and 74.

The first securing surface region 72 is delimited by the main fold line 24, the second side fold line 28, a side edge 76 extending between the second main corner 36 and the first secondary corner 42, and a side edge 78 extending between the second main corner 36 and the second secondary corner 44.

The second securing surface region 74 is delimited by the main fold line 24, a side edge 80 extending between the second secondary corner 44 and the first main corner 34, and a side edge 82 extending between the first main corner 34 and the first secondary corner 42. Furthermore, the second securing surface region 74 is delimited by the first side fold line 28. This is shown schematically in FIG. 6.

The two securing surface regions 72 and 74 overlap in a triangular area 86, which is shown schematically in FIG. 7. A base of this triangular area 86 is formed by the main fold line 24. Opposite this is a tip 84 of the area, which points in the direction toward the secondary fold line 48. The securing element 70 is arranged between the securing surface regions 72 and 74 in the region of this triangular area 86. With this securing element 70, the packaging device 10 is secured against being unfolded from the insertion position back into the starting position. The securing element 70 is configured in such a way that a strength of the connection is selected in such a way that it can be released without destroying the flat material sheet 18 upon removing the packaging device 10 from the sieve basket 12, also referred to as the aseptic presentation of the sieve basket.

Figure 13:
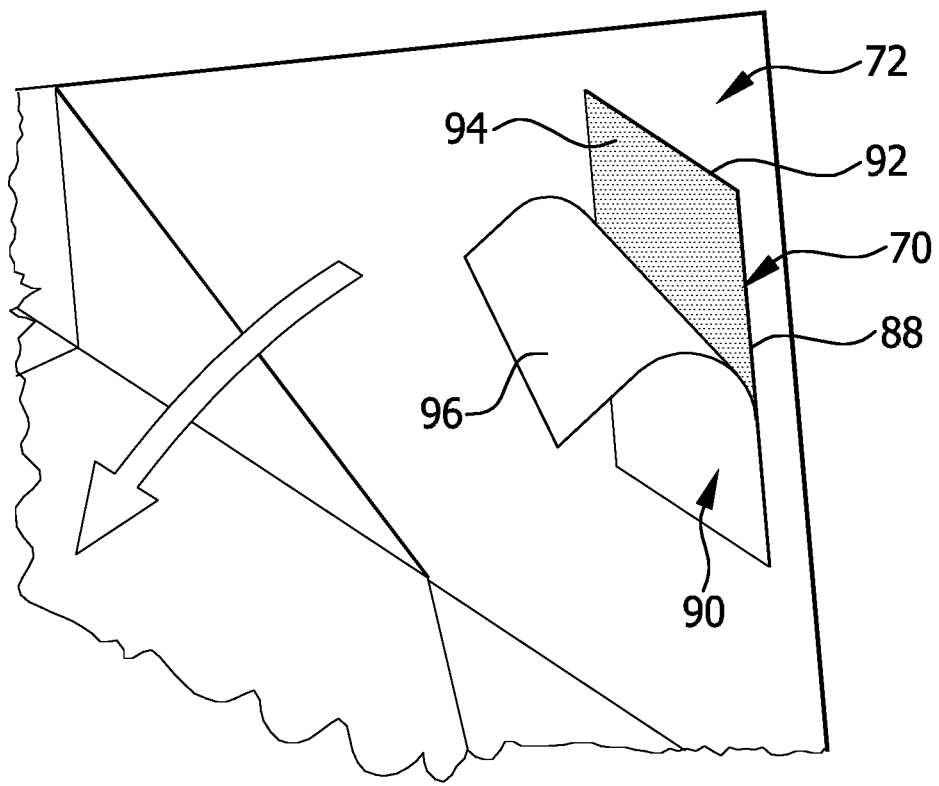
FIG. 13 shows a schematic perspective enlarged view of region A from FIG. 6.

The securing element 70 is, as schematically depicted in FIG. 13, configured in the form of a double-sided adhesive strip 88, which forms an adhesive element 90. The adhesive strip 88 has a first adhesive surface 92 and a second adhesive surface 94, which are configured facing in opposite directions.

The first adhesive surface 92 abuts against the first securing surface region 72. The second adhesive surface 94 is initially protected by a protective film 96. When the protective film 96 is peeled off, as schematically depicted in FIG. 13, the second adhesive surface 94 is uncovered and can then be brought into abutment against the second securing surface region 74 and be connected thereto.

The securing element 70 is positioned in a region of the packaging device 10 in which at least two layers, namely seven layers, formed by folding the flat material sheet 18 lie on one another in the insertion position. In an alternative embodiment, the securing element 70 is configured in the form of a welding point or an adhesive point.

Furthermore, in an analogous manner to the securing element 70, a further securing element 170 may be arranged on the first securing element surface region 72 near the first main corner 34, as schematically depicted in FIG. 5. It is then arranged on a first securing surface region 172, which cooperates with a second securing surface region 174 that is defined by a surface region of the first flat material side face 30. In an analogous manner to the second main corner 36, the first main corner 34 can be secured with the second securing element 170, namely on the flap folded about the secondary fold line 48, said flap projecting with the first secondary corner 42 partially over the main fold line 24. Thus, if the unfolding securing device 68 comprises not only the securing element 70, but also a further securing element 170 as described, a dimensional stability of the packaging device 10 can be further improved.

If the securing elements 70 and 170 are arranged in the described manner, they then lie on top of one another in the insertion position.

When the sieve basket 12 is inserted, as described, through the insertion opening 16 into the receiving space 14, the packaging device 10 can be transferred from the insertion position into a closed position. The insertion opening 16 is closed in the closed position, namely by folding a free end 98 of the packaging device 10 over the insertion opening 16, as is schematically depicted in FIG. 10. The free end 98 comprises, in particular, the portion of the packaging device 10 with the second release tab 54. The folding over of the free end 98 takes place about a closure fold line 100.

FIGS. 11 and 12 show the closed position of the packaging device 10.

So that the free end 98 does not release in an unintentional manner, it is fixed in the closed position with at least one closure element 102, namely two closure elements 102 in the embodiment depicted in the Figures.

The closure elements 102 are configured in the form of an adhesive strip 106. The closure elements 102 each define a closure element longitudinal direction 108, which runs in parallel to the two side fold lines 26 and 28.

Figure 14:
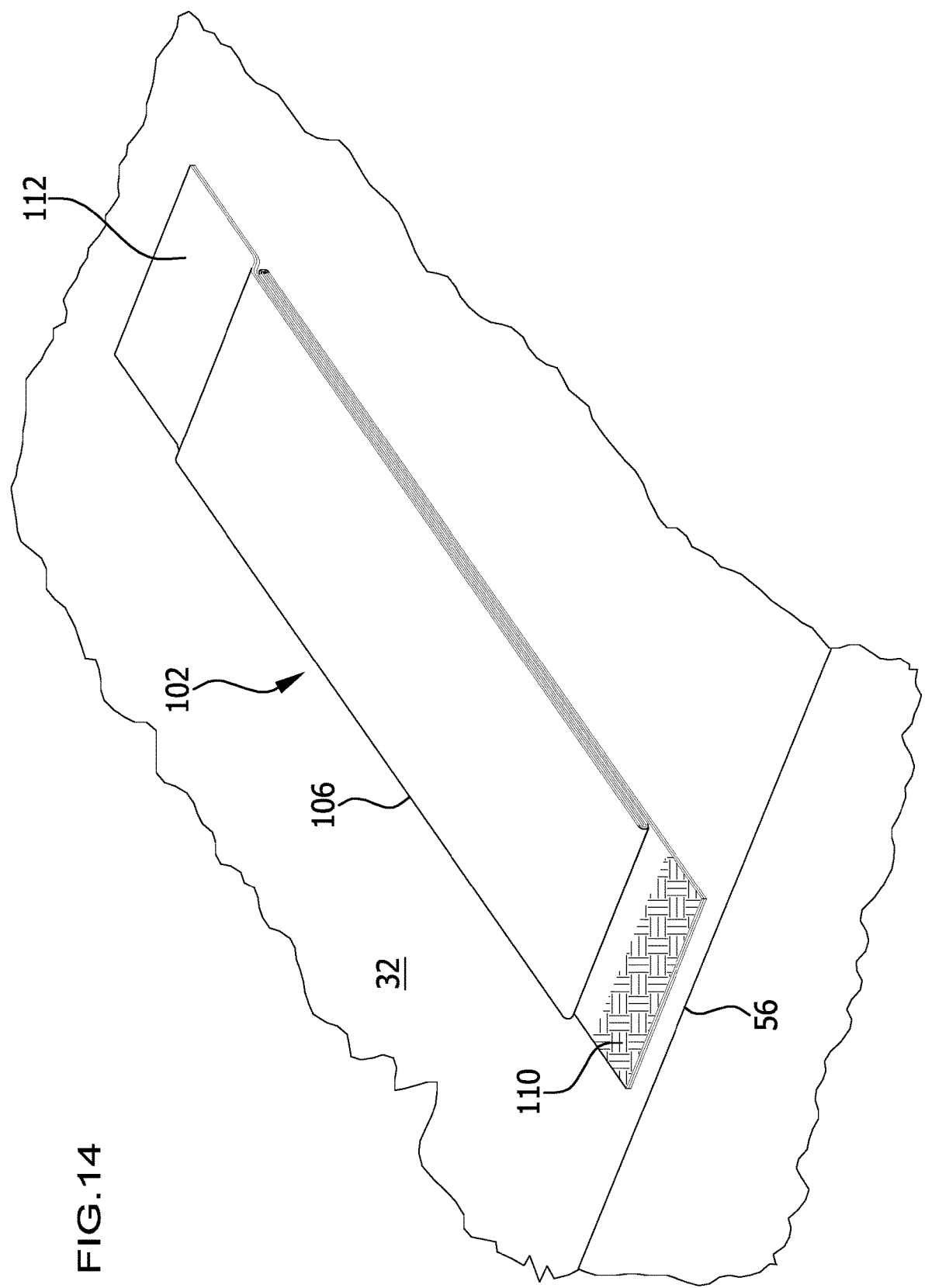
FIG. 14 shows a schematic enlarged view of region B from FIG. 11.

The closure elements 102 are configured in the form of Z-shaped adhesive strips 106 folded back on themselves, as is schematically depicted in an enlarged view in FIG. 14. The closure elements are arranged on the second flat material side face 32.

In the insertion position, i.e., before the free end 98 is fixed with the closure elements 102, the closure elements 102 extend up to the release tab main fold line 56, as is schematically depicted in FIG. 11 and in FIGS. 14 and 15.

A free pulling end 110 of the adhesive strips 106 that points in the direction toward the release tab main fold line 56 and is free of adhesive can be grasped by a user and the adhesive strip 106 can thus be pulled apart. A fastening end 112 of the adhesive strip 106 opposite the pulling end 110 is permanently connected to the second flat material side face 32. The closure element 102 pulled apart as described can then be pulled over the release tab main fold line 56 and guided around the packaging device 10 and fixed thereto, as is schematically depicted in FIG. 12.

In a further embodiment, two closure elements are alternatively or additionally provided. They are shown schematically in FIGS. 11 and 12 and are denoted with the reference numeral 104. The closure elements 104 are configured corresponding to the adhesive strips 106 and each define a closure element longitudinal direction 114, which runs in parallel to the main fold line 24. In the insertion position, the closure elements 104 extend up to one of the two side fold lines 26 or 28 and in the closed position each project over one of the two side fold lines 26 and 28 in order to laterally fix the folded over free end 98 in the closed position as described and depicted in FIG. 12.

The described embodiments depicted in the Figures are made from a flat material sheet 18, which may be, in particular, a cloth, a non-woven fabric, for example a non-woven plastic fabric, or a packaging paper, for example a crepe paper.

The packaging device 10 is configured in the form of a disposable product. Furthermore, it is sterilizable, in particular sterilizable with hot steam.

As described, the packaging device 10 is made from a one-piece, namely monolithic, flat material sheet 18.

An embodiment of a medical packaging system 116 is schematically depicted in FIG. 16. It comprises a plurality of medical packaging devices 10.

The packaging system 116 comprises a plurality of medical packaging devices 10, which differ from one another in shape and size and optionally also in the material of which the flat material sheet 18 is made.

The embodiment depicted in FIG. 16 comprises an outside packaging 118 for a plurality of packaging devices 10. The outside packaging 118 is configured in the form of a dispenser device 120 with a removal opening 122. Packaging devices 10 can be removed from the dispenser device 120 through the removal opening 122.

The packaging system 116 optionally comprises further dispenser devices 120 in each of which identical packaging devices 10 are accommodated. If, for example, three different sizes of sieve baskets 12 are to be packaged, then preferably three dispenser devices 120 are provided, which each contain a plurality of identical packaging devices 10, wherein the dispenser devices 120 are adapted to the size and shape of the packaging devices 10 for the three different sieve baskets 12. Therefore, for example three differently sized dispenser devices 120 may be provided.

The described embodiments of medical packaging devices 10 and the described embodiments of packaging systems 116 make it possible, in particular, to quickly and efficiently package sieve baskets 12. In particular, it is not necessary to teach a user a certain folding technique for wrapping the sieve basket 12 in a flat material sheet 18. Instead, a user can simply slide the sieve basket 12 through the insertion opening 16 into the receiving space 14 of the packaging device 10 and then close same by folding the free end 98 over the insertion opening 16. In this way, significant time savings in packaging the sieve baskets 12 with packaging devices 10 in the form of soft packaging can be achieved, thereby also resulting in cost savings.

A reproducibility in the packaging of the sieve baskets 12 can also be significantly increased as a result of the packaging devices 10 being provided preassembled. A training expenditure for staff that packages the sieve baskets 12 is also significantly reduced.

What is claimed is:

1. A medical packaging device for sterile packaging of a sieve basket, wherein the packaging device defines a receiving space for accommodating a sieve basket in a packaging position and an insertion opening for inserting a sieve basket into the receiving space, wherein the insertion opening is open in an insertion position, wherein the packaging device is made from a flat material sheet that is unfolded in a starting position by folding multiple times, wherein the receiving space in the insertion position has two abutting receiving space flat material sheet surface regions, which are delimited by at least three fold lines of the flat material sheet in such a way that the receiving space is closed on all sides except for the insertion opening, wherein the packaging device comprises an unfolding securing device for securing the packaging device in the insertion position against being completely unfolded back into the starting position.

2. The medical packaging device in accordance with claim 1, wherein at least one of:
   a) the flat material sheet defines a first flat material side face and a second flat material side face, wherein the first flat material side face and the second flat material side face face in opposite directions in the starting position, and wherein the first flat material side face comprises the two abutting receiving space flat material sheet surface regions;
   and
   b) the packaging device in the insertion position comprises at least three fold lines;
   and
   c) the flat material sheet in the starting position is of a quadrangular configuration;
   and
   d) one of the at least three fold lines is configured in the form of a main fold line and wherein the main fold line connects two main corners of the flat material sheet that are located opposite one another in the starting position.

3. The medical packaging device in accordance with claim 1, wherein the flat material sheet in the starting position comprises two opposing secondary corners, wherein the two secondary corners lie on one another in a first folded position in which the flat material sheet is folded from the starting position about the main fold line, wherein the packaging device comprises a first release tab, wherein the first release tab is formed by folding back a first one of the two secondary corners from the first folded position into a second folded position about a secondary fold line, and wherein the secondary fold line runs in parallel or substantially in parallel to the main fold line and extends between the main fold line and the secondary corners in the first folded position.

4. The medical packaging device in accordance with claim 3, wherein a first one of the two main corners is folded from the second folded position about a first one of the two side fold lines in the direction toward a second one of the two main corners into a third folded position and wherein the second one of the two main corners is folded from the third folded position into a fourth folded position about a second one of the two side fold lines in the direction toward the first one of the two side fold lines.

5. The medical packaging device in accordance with claim 1, wherein the unfolding securing device comprises at least one securing element for securing the packaging device in the insertion position.

6. The medical packaging device in accordance with claim 1, wherein the packaging device comprises at least one closure element for closing the packaging device in a packaging position in which the insertion opening is closed by folding the second secondary corner about a closure fold line in the direction toward the first secondary corner.

7. The medical packaging device in accordance with claim 6, wherein at least one of:
   a) the at least one closure element is configured in the form of an adhesive strip;
   and
   b) the at least one closure element is arranged or formed on the second flat material side face;
   and
   c) the at least one closure element defines a closure element longitudinal direction and wherein the closure element longitudinal direction runs in parallel or substantially in parallel to one of the two side fold lines or in parallel or substantially in parallel to the main fold line;
   and
   d) the insertion position the at least one closure element extends up to the release tab main fold line or up to one of the two side fold lines and in the closed position the at least one closure element extends over the release tab main fold line or over one of the two side fold lines.

8. The medical packaging device in accordance with claim 1, wherein at least one of:
   a) the flat material sheet is made of a cloth, a non-woven fabric or a packaging paper;
   and
   b) the packaging device is configured in the form of a disposable product;
   and
   c) the packaging device is configured to be sterilizable;
   and
   d) the packaging device is made from a one-piece flat material sheet.

9. A medical packaging system for sieve baskets comprising a plurality of medical packaging devices, wherein at least one of the plurality of medical packaging devices is in the form of a medical packaging device for sterile packaging of a sieve basket, wherein the packaging device defines a receiving space for accommodating a sieve basket in a packaging position and an insertion opening for inserting a sieve basket into the receiving space, wherein the insertion opening is open in an insertion position, wherein the packaging device is made from a flat material sheet that is unfolded in a starting position by folding multiple times, wherein the receiving space in the insertion position has two abutting receiving space flat material sheet surface regions, which are delimited by at least three fold lines of the flat material sheet in such a way that the receiving space is closed on all sides except for the insertion opening, wherein the packaging device comprises an unfolding securing device for securing the packaging device in the insertion position against being completely unfolded back into the starting position.

10. The medical packaging system in accordance with claim 9, wherein at least one of:
   a) at least two of the plurality of medical packaging devices differ from one another at least one of in shape and size and in the material of which the flat material sheet is made;
   and
   b) the packaging system comprises an outer packaging for the plurality of packaging devices;
   and
   c) that the packaging system comprises at least one sieve basket.

11. A method for producing a medical packaging device for sterile packaging of a sieve basket, wherein the packaging device is configured with a receiving space for accommodating a sieve basket in a packaging position and an insertion opening for inserting a sieve basket into the receiving space, wherein the insertion opening is open in an insertion position, wherein the packaging device is made from a flat material sheet that is unfolded in a starting position by folding multiple times, wherein the receiving space in the insertion position has two abutting receiving space flat material sheet surface regions, which are delimited by at least three fold lines of the flat material sheet in such a way that the receiving space is closed on all sides except for the insertion opening, wherein the packaging device is secured in the insertion position against being completely unfolded back into the starting position.

12. The method in accordance with claim 11, wherein at least one of
   a) the flat material sheet defines a first flat material side face and a second flat material side face, wherein the first flat material side face and the second flat material side face face in opposite directions in the starting position, and wherein the two abutting receiving space flat material sheet surface regions are formed from the first flat material side face by folding the flat material sheet;
   and
   b) the packaging device is formed by folding the flat material sheet along at least three fold lines;
   and
   c) a flat material sheet is provided, which in the starting position is of a quadrangular configuration;
   and
   d) one of the at least three fold lines is configured in the form of a main fold line, which connects two main corners of the flat material sheet that are located opposite one another in the starting position.

13. The method in accordance with claim 11, wherein the flat material sheet in the starting position comprises two opposing secondary corners, wherein the two secondary corners are brought into a first folded position by folding the flat material sheet from the starting position about the main fold line, in which first folded position they lie on one another, wherein a first release tab of the packaging device is formed by folding back a first one of the two secondary corners about a secondary fold line from the first folded position into a second folded position, and wherein the secondary fold line runs in parallel or substantially in parallel to the main fold line and extends between the main fold line and the secondary corners in the first folded position.

14. The method in accordance with claim 13, wherein a first one of the two main corners is folded from the second folded position about a first one of the two side fold lines in the direction toward a second one of the two main corners into a third folded position and wherein the second one of the two main corners is folded from the third folded position into a fourth folded position about a second one of the two side fold lines in the direction toward the first one of the two side fold lines.

15. The method in accordance with claim 14, wherein a second release tab of the packaging device is formed by folding a second one of the two secondary corners, which in the insertion position points away from the insertion opening, from the fourth folded position into a fifth folded position about a release tab main fold line in the direction toward the main fold line and by folding back the second secondary corner from the fifth folded position into a sixth folded position about a release tab secondary fold line in a direction away from the main fold line.

16. The method in accordance with claim 11, wherein the packaging device is secured in the insertion position with at least one securing element.

17. The method in accordance with claim 16, wherein at least one of:
   a) the packaging device defines at least one first securing surface region and at least one second securing surface region, wherein the first securing surface region and the second securing surface region are different from the two abutting receiving space flat material sheet surface regions that abut against one another in the insertion position, wherein the first securing surface region and the second securing surface region abut against one another in the insertion position, and wherein the at least one first securing surface region and the at least one second securing surface region are connected to one another at least one of in a force-locking and materially bonded manner, with the at least one securing element;
   and
   b) the at least one securing element is formed by a welding point, by an adhesive, or by an adhesive element,
   and
   c) the at least one securing element is positioned in a region of the packaging device in which at least two layers formed by folding the flat material sheet lie on one another in the insertion position.

18. The method in accordance with claim 11, wherein the packaging device is configured having at least one closure element for closing the packaging device in a packaging position in which the insertion opening is closed by folding the second secondary corner about a closure fold line in the direction toward the first secondary corner.

19. The method in accordance with claim 11, wherein at least one of:
   a) the flat material sheet is made of a cloth, a non-woven fabric, or a packaging paper;
   and
   b) the packaging device is configured as a disposable product;
   and
   c) the packaging device is configured to be sterilizable;
   and
   d) the packaging device is made from a one-piece flat material sheet.

* * * * *